(12) United States Patent
Steines et al.

(10) Patent No.: US 12,019,314 B1
(45) Date of Patent: Jun. 25, 2024

(54) HEAD MOUNTED DISPLAY ASSEMBLY WITH CONTROL OF HEAD MOUNTED DISPLAY AND LOUPE POSITION AND ORIENTATION

(71) Applicant: OnPoint Medical, Inc., Franconia, NH (US)

(72) Inventors: Daniel Steines, Lexington, MA (US); Chuang-Jang Chiou, Bedford, MA (US); Raymond Bojarski, Attleboro, MA (US); Philipp K. Lang, Franconia, NH (US)

(73) Assignee: OnPoint Medical, Inc., Franconia, NH (US)

( * ) Notice: Subject to any disclaimer, the term of this patent is extended or adjusted under 35 U.S.C. 154(b) by 0 days.

(21) Appl. No.: 18/472,121

(22) Filed: Sep. 21, 2023

Related U.S. Application Data

(60) Provisional application No. 63/376,453, filed on Sep. 21, 2022.

(51) Int. Cl.
| | |
|---|---|
| *G02C 7/08* | (2006.01) |
| *A61B 90/00* | (2016.01) |
| *A61B 90/25* | (2016.01) |
| *A61B 90/50* | (2016.01) |
| *G02B 27/01* | (2006.01) |

(52) U.S. Cl.
CPC ............. *G02C 7/088* (2013.01); *A61B 90/25* (2016.02); *A61B 90/37* (2016.02); *G02B 27/0172* (2013.01); *A61B 2090/372* (2016.02); *A61B 2090/502* (2016.02); *G02B 2027/0178* (2013.01)

(58) Field of Classification Search
USPC .......................................................... 345/8
See application file for complete search history.

(56) References Cited

U.S. PATENT DOCUMENTS

| | | | |
|---|---|---|---|
| 11,006,093 B1* | 5/2021 | Hegyi ........................ G06T 7/50 |
| 2007/0064307 A1* | 3/2007 | Hluchan .................... G02C 7/12 351/158 |
| 2014/0146153 A1* | 5/2014 | Birnkrant ................. H04N 7/18 348/77 |
| 2016/0054571 A1* | 2/2016 | Tazbaz ............... G02B 27/0176 359/630 |
| 2016/0334644 A1* | 11/2016 | Garofolo .............. G02B 27/017 |
| 2017/0315536 A1* | 11/2017 | Brusky .................. B25J 9/1676 |
| 2017/0322410 A1* | 11/2017 | Watson ................. G06T 19/006 |
| 2017/0340405 A1* | 11/2017 | Aferzon ................. A61B 90/50 |
| 2018/0101030 A1* | 4/2018 | Ton ......................... G02C 5/045 |
| 2018/0286136 A1* | 10/2018 | Jones .................... G06F 3/0346 |
| 2019/0254754 A1* | 8/2019 | Johnson ............... G06T 19/006 |
| 2020/0117025 A1* | 4/2020 | Sauer ....................... G02C 9/00 |
| 2021/0338370 A1* | 11/2021 | Bryant ................... A61B 90/50 |
| 2023/0088437 A1* | 3/2023 | Hauger ................. A61B 90/37 250/225 |

* cited by examiner

*Primary Examiner* — Chineyere D Wills-Burns
(74) *Attorney, Agent, or Firm* — Greenberg Traurig, LLP; Natalie Salem; Barry Schindler

(57) ABSTRACT

Systems, devices, techniques and methods for concurrent use of head mounted displays with surgical loupes during surgical procedures are provided. In some embodiments, the head mounted display comprises a display unit with a combiner and the surgical loupe is mounted below the display unit. In some embodiments, eye relief from the back side of the combiner to the front surface of the cornea is the same or smaller than a vertex distance from the back lens of the surgical loupe to the front surface of the cornea.

16 Claims, 24 Drawing Sheets

HEAD MOUNTED DISPLAY ASSEMBLY WITH CONTROL OF HEAD MOUNTED DISPLAY AND LOUPE POSITION AND ORIENTATION

RELATED APPLICATIONS

This application claims the benefit of and priority to U.S. Provisional Application Ser. No. 63/376,453, filed Sep. 21, 2022, the entire content of which is incorporated herein by reference in its entirety.

TECHNICAL FIELD

The present disclosure relates to systems, devices and methods for performing a surgical procedure with visual guidance using an optical head mounted display and surgical loupes.

BACKGROUND

With surgical interventions or procedures, many surgeons like to use surgical loupes to magnify select parts of a patient's anatomy, e.g. a brain, an organ, a heart, an abdomen, a spine, a bone and/or a joint.

SUMMARY

According to some embodiments, devices, systems, methods and techniques for performing a surgical procedure with visual guidance using an optical head mounted display and surgical loupes.

In some embodiments, the system comprises a head mounted display (HMD), and a surgical loupe. In some embodiments, the head mounted display comprises a display unit with a combiner. In some embodiments, the surgical loupe is mounted below the display unit of the head mounted display. In some embodiments, eye relief from the back side of the combiner to the front surface of the cornea is the same or smaller than a vertex distance from the back lens of the surgical loupe to the front surface of the cornea.

In some embodiments, the system comprises a head mounted display (HMD), and a surgical loupe, the head mounted display comprising a display unit with a combiner, wherein the surgical loupe is mounted below the display unit of the head mounted display, and wherein eye relief from a back side of the combiner to a front surface of a cornea is the same or smaller than a vertex distance from a back lens of the surgical loupe to the front surface of the cornea.

In some embodiments, the surgical loupe is attached to the head mounted display, to a head mount, or to a head band.

In some embodiments, the display unit of the HMD comprises at least one LED display, OLED display, optical element, electronic element, the combiner or combination thereof.

In some embodiments, the combiner comprises a mirror, a halftone mirror, a curved mirror, a waveguide or combination thereof.

In some embodiments, the display unit is configured to generate, display, and/or reflect a virtual display. In some embodiments, the virtual display is a 2D display, a 3D display, a non-stereoscopic display, a stereoscopic display, or a combination thereof. In some embodiments, the virtual display comprises a 2D image of an anatomic structure of a patient, a 3D image of an anatomic structure of a patient, a virtual tool, a virtual instrument, a virtual implant, a virtual device, or a combination thereof.

In some embodiments, the system further comprises an attachment mechanism, wherein the attachment mechanism is configured to attach the surgical loupe to the head mounted display, the head mount or the head band. In some embodiments, the attachment mechanism is configured to move the loupe into at least a first and a second position in relationship to the head mounted display. In some embodiments, the first position is configured to facilitate viewing through the surgical loupe, wherein the second position is configured to place the loupe outside the visual field of a user wearing the system.

Aspects of the disclosure relate to system comprising: a head mounted display; and a surgical loupe, wherein the head mounted display comprises a display unit with a left combiner for a left eye and a display unit with a right combiner for a right eye, wherein the surgical loupe comprises a left surgical loupe for the left eye and a right surgical loupe for the right eye, wherein the left surgical loupe is mounted below the left eye display unit and the right surgical loupe below the right eye display unit of the head mounted display, and wherein an eye relief from a back side of the left combiner to a front surface of a left cornea is the same or smaller than a vertex distance from a back lens of the left loupe to the front surface of the left cornea, and/or wherein an eye relief from a back side of the right combiner to the front surface of a right cornea is the same or smaller than a vertex distance from a back lens of the right loupe to a front surface of the right cornea.

In some embodiments, the left surgical loupe and the right surgical loupe are attached to the head mounted display, to a head mount, or to a head band.

In some embodiments, each display unit of the HMD comprises at least one LED display, OLED display, optical element, electronic element, or combination thereof.

In some embodiments, each combiners comprises a mirror, a halftone mirror, a curved mirror, a waveguide or combination thereof.

In some embodiments, each display unit is configured to generate, display, and/or reflect a virtual display. In some embodiments, the virtual display is a 2D display, a 3D display, a non-stereoscopic display, a stereoscopic display, or a combination thereof. In some embodiments, the virtual display comprises a 2D image of an anatomic structure of a patient, a 3D image of an anatomic structure of a patient, a virtual tool, a virtual instrument, a virtual implant, a virtual device, or a combination thereof.

In some embodiments, the system further comprises one or more attachment mechanism, wherein the one or more attachment mechanism is configured to attach the left surgical loupe and the right surgical loupe to the head mounted display, the head mount or the head band. In some embodiments, the one or more attachment mechanism is configured to move the left surgical loupe into at least a first and a second position in relationship to the head mounted display, and/or to move the right surgical loupe into at least a first and a second position in relationship to the head mounted display. In some embodiments, the first position is configured to facilitate viewing through the left surgical loupe and/or the right surgical loupe, wherein the second position is configured to place the left surgical loupe and/or the right surgical outside the visual field of a user wearing the system.

BRIEF DESCRIPTION OF THE DRAWINGS

Illustrative, non-limiting example embodiments will be more clearly understood from the following detailed description taken in conjunction with the accompanying drawings.

FIG. 3G, FIG. 3H and FIG. 3I illustrate an HMD used in conjunction with a surgical loupe, with the HMD shown in different positions relative to the user's eye, according to various embodiments.

DETAILED DESCRIPTION

Figure 1A:
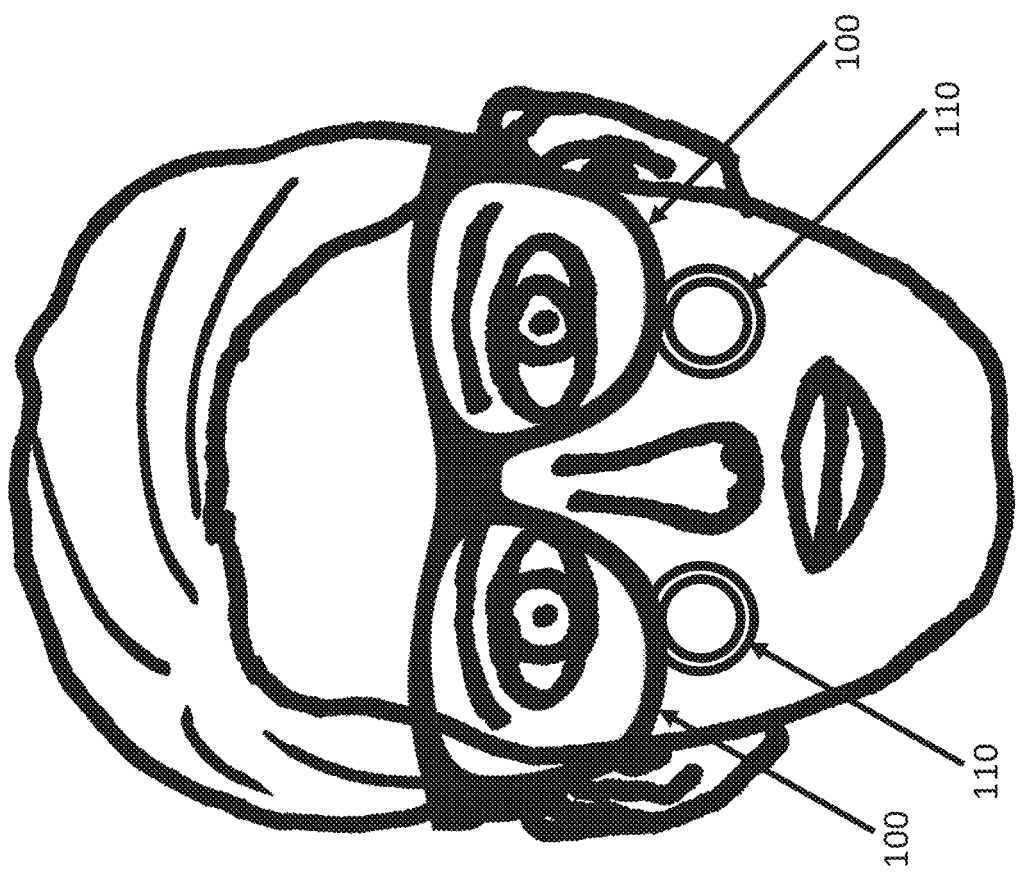
FIG. 1A illustrates a surgical loupe mounted below a head mounted display (HMD) according to various embodiments.

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It will be understood that various changes may be made in the function and arrangement of elements without departing from the spirit and scope of the presently disclosed embodiments.

Specific details are given in the following description to provide a thorough understanding of the embodiments. However, it will be understood by one of ordinary skill in the art that the embodiments may be practiced without these specific details.

Subject matter will now be described more fully with reference to the accompanying drawings, which form a part hereof, and which show, by way of illustration, specific example aspects and embodiments of the present disclosure. Subject matter may, however, be embodied in a variety of different forms and, therefore, covered or claimed subject matter is intended to be construed as not being limited to any example embodiments set forth herein; example embodiments are provided merely to be illustrative. The following detailed description is, therefore, not intended to be taken in a limiting sense.

Head mounted displays provide the opportunity to generate virtual displays comprising, for example, 2D or 3D scans of the patient and/or virtual surgical guides, virtual tools, virtual implants or devices, to guide a surgeon during the procedure.

Some aspects of the disclosure relate to systems, devices, techniques and methods enabling concurrent use of surgical loupes and HMD displays. Some aspects of the disclosure relate to system comprising a head mounted display (HMD) and a surgical loupe. In some embodiments, an head mounted display assembly with control of head mounted display and loupe position and orientation is provided.

In some embodiments, the head mounted display comprises a display unit with a combiner. In some embodiments, the surgical loupe is mounted below the display unit of the head mounted display. In some embodiments, the system is configured so that an eye relief from the back side of the combiner to the front surface of the cornea is the same or smaller than a vertex distance from the back lens of the surgical loupe to the front surface of the cornea.

In some embodiments of the disclosure, a surgeon can use a surgical loupe in conjunction with use of a head mounted display (HMD), e.g. a video see through HMD or an optical see through HMD. In some embodiments, the HMD is an optical see through HMD. In other embodiments, the HMD is a video see through HMD.

Exemplary optical head mounted displays include the ODG R-7, R-8 and R-8 smart glasses from ODG (Osterhout Group, San Francisco, CA), the NVIDIA 942 3-D vision wireless glasses (NVIDIA, Santa Clara, CA) the Microsoft HoloLens (Microsoft, Redmond, WI), the Daqri Smart Glass (Daqri, Los Angeles, CA) the Metal (Meta Vision, San Mateo, CA), the Moverio BT-300 (Epson, Suwa, Japan), the Blade 3000 and the Blade M300 (Vuzix, West Henrietta, NY).

The Microsoft HoloLens is manufactured by Microsoft. It is a pair of augmented reality smart glasses. Hololens is a see through optical head mounted display. Hololens can use the Windows 10 operating system. The front portion of the Hololens includes, among others, sensors, related hardware, several cameras and processors. The visor includes a pair of transparent combiner lenses, in which the projected images are displayed. The HoloLens can be adjusted for the interpupillary distance (IPD) using an integrated program that recognizes gestures. A pair of speakers is also integrated. The speakers do not exclude external sounds and allow the user to hear virtual sounds. A USB 2.0 micro-B receptacle is integrated. A 3.5 mm audio jack is also present. The HoloLens has an inertial measurement unit (IMU) with an accelerometer, gyroscope, and a magnetometer, four environment mapping sensors/cameras (two on each side), a depth camera with a 120°×120° angle of view, a 2.4-megapixel photographic video camera, a four-microphone array, and an ambient light sensor. Hololens has an Intel Cherry Trail SoC containing the CPU and GPU. HoloLens includes also a custom-made Microsoft Holographic Processing Unit (HPU). The SoC and the HPU each have 1 GB LPDDR3 and share 8 MB SRAM, with the SoC also controlling 64 GB eMMC and running the Windows 10 operating system. The HPU processes and integrates data from the sensors, as well as handling tasks such as spatial mapping, gesture recognition, and voice and speech recognition. HoloLens includes a IEEE 802.11ac Wi-Fi and Bluetooth 4.1 Low Energy (LE) wireless connectivity. The headset uses Bluetooth LE and can connect to a clicker, a finger-operating input device that can be used for selecting menus and functions.

A number of applications are available for Microsoft Hololens, for example a catalogue of holograms, HoloStudio, a 3D modelling application by Microsoft with 3D print capability, Autodesk Maya 3D creation application, FreeForm, integrating HoloLens with the Autodesk Fusion 360 cloud-based 3D development application, and others. HoloLens utilizing the HPU can employ sensual and natural interface commands—voice, gesture, and gesture. Gaze commands, e.g. head-tracking, allows the user to bring application focus to whatever the user is perceiving. Any virtual application or button can be selected using an air tap method, similar to clicking a virtual computer mouse. The tap can be held for a drag simulation to move a display. Voice commands can also be utilized. The HoloLens shell utilizes many components or concepts from the Windows desktop environment. A bloom gesture for opening the main menu is performed by opening one's hand, with the palm facing up and the fingers spread. Windows can be dragged to a particular position, locked and/or resized. Virtual windows or menus can be fixed at locations or physical objects. Virtual windows or menus can move with the user or can be fixed in relationship to the user. Or they can follow the user as he or she moves around. The Microsoft HoloLens App for Windows 10 PC's and Windows 10 Mobile devices can be used by developers to run apps and to view live stream from the HoloLens user's point of view, and to capture augmented reality photos and videos. Almost all Universal Windows Platform apps can run on Hololens. These apps can be projected in 2D. Select Windows 10 APIs are currently supported by HoloLens. Hololens apps can also be developed on Windows 10 PC's.

Holographic applications can use Windows Holographic APIs. Unity (Unity Technologies, San Francisco, CA) and Vuforia (PTC, Inc., Needham, MA) are some apps that can be utilized. Applications can also be developed using DirectX and Windows API's.

Computer Graphics Viewing Pipeline

In some embodiments, the optical head mount display uses a computer graphics viewing pipeline that consists of the following steps to display 3D objects or 2D objects positioned in 3D space or other computer-generated objects and models:
 1. Registration
 2. View projection Registration:

The different objects to be displayed by the HMD computer graphics system (for instance virtual anatomical models, virtual models of instruments, geometric and surgical references and guides) are initially all defined in their own independent model coordinate system. During the registration process, spatial relationships between the different objects are defined, and each object is transformed from its own model coordinate system into a common global coordinate system. Different techniques that are described below can be applied for the registration process. For augmented reality HMDs that superimpose computer-generated objects with live views of the physical environment, the global coordinate system is defined by the environment. A process called spatial mapping, described below, creates a computer representation of the environment that allows for merging and registration with the computer-generated objects, thus defining a spatial relationship between the computer-generated objects and the physical environment.

View Projection:

Once all objects to be displayed have been registered and transformed into the common global coordinate system, they are prepared for viewing on a display by transforming their coordinates from the global coordinate system into the view coordinate system and subsequently projecting them onto the display plane. This view projection step uses the viewpoint and view direction to define the transformations applied in this step. For stereoscopic displays, such as an HMD, two different view projections can be used, one for the left eye and the other one for the right eye. For augmented reality HMD the position of the viewpoint and view direction relative to the physical environment can be known to correctly superimpose the computer-generated objects with the physical environment. As the viewpoint and view direction change, for example due to head movement, the view projections are updated so that the computer-generated display follows the new view.

Positional Tracking Systems

In certain embodiments, the position and/or orientation of the HMD can be tracked. For example, in order to calculate and update the view projection of the computer graphics view pipeline as described in the previous section and to display the computer-generated overlay images in the HMD, the view position and direction needs to be known.

Different methods to track the HMD can be used. For example, the HMD can be tracked using outside-in tracking. For outside-in tracking, one or more external sensors or cameras can be installed in a stationary location, e.g. on the ceiling, the wall or on a stand. The sensors or camera capture the movement of the HMD, for example through shape detection or markers attached to the HMD or the user's head. The sensor data or camera image is typically processed on a central computer to which the one or more sensors or cameras are connected. The tracking information obtained on the central computer is then used to compute the view projection. The view projection can be computed on the central computer or on the HMD.

In another embodiment, the inside-out tracking method is employed. One or more sensors or cameras are attached to the HMD or the user's head or integrated with the HMD. The sensors or cameras can be dedicated to the tracking functionality. In other embodiments, the data collected by the sensors or cameras is used for positional tracking as well as for other purposes, e.g. image recording or spatial mapping. Information gathered by the sensors and/or cameras is used to determine the HMD's position and orientation in 3D space. This can be done, for example, by detecting optical, infrared or electromagnetic markers attached to the external environment. Changes in the position of the markers relative to the sensors or cameras are used to continuously determine the position and orientation of the HMD. Data processing of the sensor and camera information is typically performed by a mobile processing unit attached to or integrated with the HMD, which allows for increased mobility of the HMD user as compared to outside-in tracking. Alternatively, the data can be transmitted to and processed on the central computer.

Inside-out tracking can also utilize markerless techniques. For example, spatial mapping data acquired by the HMD sensors can be aligned with a virtual model of the environment, thus determining the position and orientation of the HMD in the 3D environment. Alternatively, or additionally, information from inertial measurement units can be used. Potential advantages of inside-out tracking include greater mobility for the HMD user, a greater field of view not limited by the viewing angle of stationary cameras and reduced or eliminated problems with marker occlusion. HMD tracking can also be performed using inertial measurement units (IMUS), for example integrated or attached to the HMD or a head mount.

In some embodiments, a surgical loupe can be configured for binocular use, with a left eye lens or lenses or optical system and a right eye lens or lenses or optical system. The distance between the left eye lens, lenses, or optical system and the right eye lens, lenses, or optical system can be adjusted for a user's (e.g. a surgeon) interpupillary distance. The adjustment can be performed, for example, using a mechanical adjustment means, e.g. via one or more members connecting the left and right eye lens, lenses, or optical system, for example in a slidably engageable fashion. In some embodiments, for example when an electronic magnified display (as an electronic loupe), e.g. for the left eye and/or the right eye is used, for example in conjunction with a head mounted display, optionally displayed by the head mounted display, the adjustment can be made by electronic means, e.g. by shifting the left eye display so as to center it over the left pupil and/or by shifting the right eye display so as to center it over the right pupil.

The optical elements of loupes can be available or adjusted for different focal lengths depending on the distance from the surgeon's eyes to the patient or an anatomic structure of the patient. Surgical loupes can be provided with different magnifications, e.g. 1.5×, 2.0×, 2.5×, 3.0×, 3.5×, 4.0×, 5.0×, 6.0×, 7.0× or any other value. Magnification can be continuous, for example when loupes with zoom optics are used. Electronic loupes and or magnification, e.g. integrated into an HMD, can have different electronic magnification levels, e.g. 1.5×, 2.0×, 2.5×, 3.0×, 3.5×, 4.0×, 5.0×, 6.0×, 7.0× or any other value.

A surgical loupe can be attached to a head mount, e.g. in a non-limiting, exemplary fashion a head mount 210 (FIGS. 2A-2F), a head band, e.g. head band attached or mounted loupes, or attached or mounted to a head mounted display (HMD). The attachment can comprise one or more locking mechanisms, locking screws and the like. The attachment can be configured to be adjustable, e.g. mounting the surgical loupe at different positions, angles, orientations relative to an HMD and/or the front surface of a user's cornea(s). The attachment can be configured to move the surgical loupes into one or more, two or more positions. The attachment can be configured to move the surgical loupes into a first position, e.g. below the HMD and for looking through the HMD or the loupes, and a second position, e.g. above the HMD with the loupes moved out of the way, not available for looking through.

In some embodiments, the position and/or orientation of a loupe and/or an HMD can be adjusted and/or optimized in relationship to the optical axis and/or the visual axis of the eye, which is also referred herein as the pupillary axis and the line of sight, respectively. As used herein, the optical axis is composed of an imaginary line perpendicular to the cornea that intersects the center of the entrance pupil. As used herein, the visual axis is an imaginary line that connects an object, e.g. a surgical site, a joint, a spine, an anatomic structure, an anatomic landmark, in space, the center of the entrance and exit pupil, and the center of the fovea.

Figure 1B:
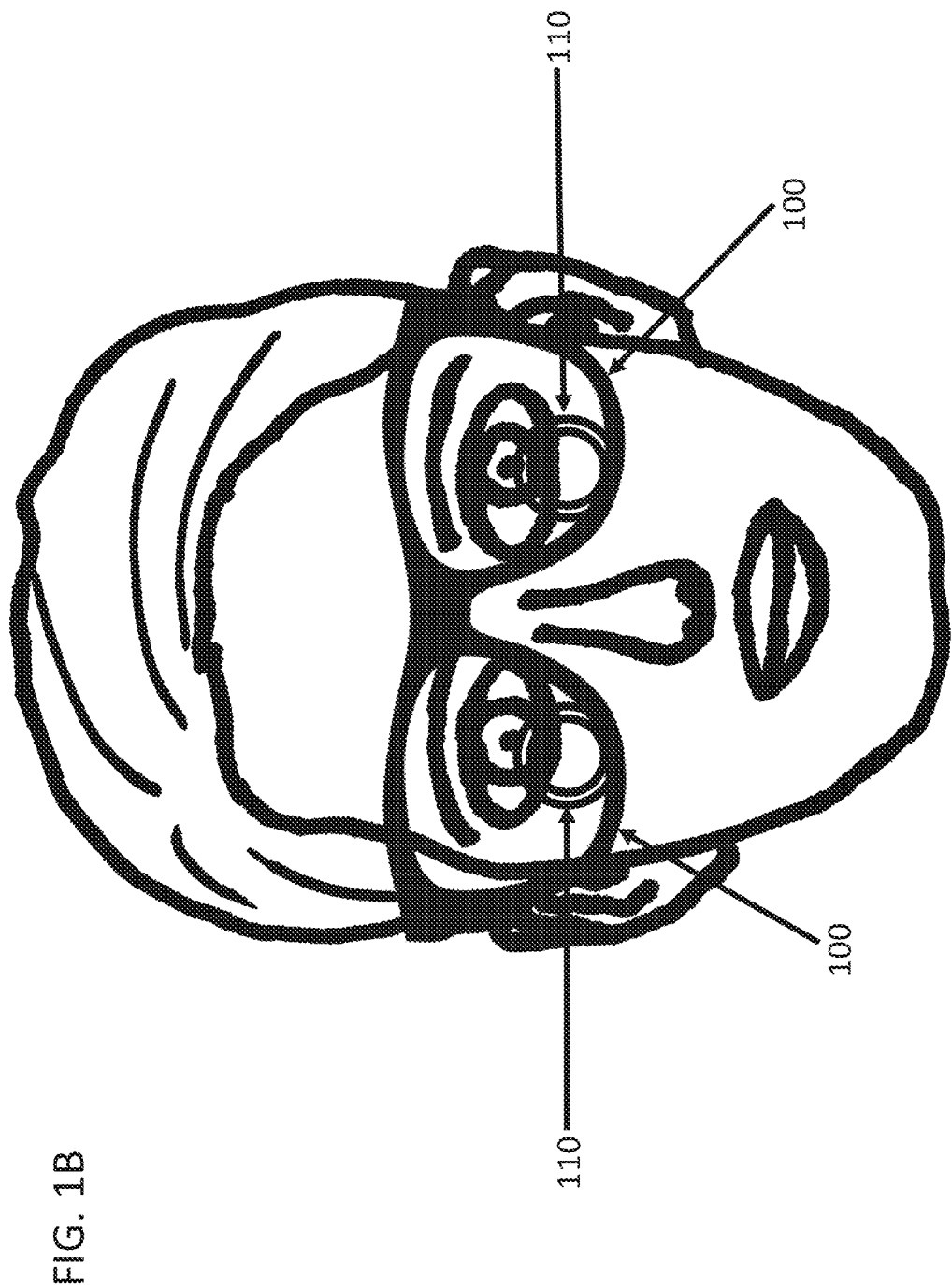
FIG. 1B illustrates a surgical loupe positioned in front of a head mounted display (HMD) according to various embodiments.

In some embodiments, a loupe 110 can be positioned below an HMD 100 (FIG. 1A). In some embodiments, a loupe 110 can be positioned in front of an HMD 100 (FIG. 1B), e.g. attached to the rim or house of an HMD or attached to an external facing lens or optical element.

In some embodiments, an HMD display or HMD display unit comprises a combiner, an LED display, an OLED display, optical elements, electronic elements, or a combination thereof.

In some of the embodiments, a combiner comprises a mirror, a halftone mirror, a curved mirror, other mirrors, a waveguide or a combination thereof.

In some embodiments, one or more of the following can be adjusted, modified, changed, or moved, e.g. alone or in combination, with regard to loupe position and/or orientation and/or HMD position and/or orientation:

Distance of loupe to cornea, pupil, retina, fovea (e.g. first lens to cornea, pupil, retina, fovea, last or back lens to cornea, pupil, retina, fovea, closest (or back) lens to cornea, pupil, retina, fovea, furthest lens to cornea, pupil, retina, fovea, any lens to pupil, cornea, retina, fovea)

Angle of loupe in relationship to cornea, pupil, retina, fovea, e.g. when looking straight, e.g. for a given head position Angle of loupe, including optical axis of loupe, in relationship to optical axis and/or visual axis of eye, e.g. when looking straight, e.g. for a given head position Angle of optical axis of loupe in relationship to cornea, pupil, retina, fovea, e.g. when looking straight Angle of optical axis of loupe in relationship to optical axis and/or visual axis of eye, e.g. when looking straight, e.g. for a given head position Height/position of loupe in relationship to cornea, pupil, retina, fovea, e.g. how many mm inferior to pupil, cornea, retina, fovea (e.g. how many mm from center of first lens to pupil, cornea, retina, fovea, center of last lens to pupil, cornea, retina, fovea, center of closest lens to pupil, cornea, retina, fovea, center of furthest lens to pupil, cornea, retina, fovea, center of any lens to pupil, cornea, retina, fovea)

Distance of loupe to HMD, HMD display unit (e.g. center or rim or any other portion) or HMD frame (e.g. first loupe lens to HMD display, last or back lens of loupe to HMD display, closest loupe lens to HMD display, furthest loupe lens to HMD display Angle of loupe in relationship to HMD display Height/position/orientation of loupe in relationship to HMD display Angle of optical axis of loupe in relationship to HMD display Height/position/orientation of optical axis of loupe in relationship to HMD display Angle of optical axis of loupe in relationship to center of HMD display Height/position/orientation of optical axis of loupe in relationship to center of HMD display Angle of optical axis of loupe in relationship to optical axis of HMD display Height/position/orientation of optical axis of loupe in relationship to optical axis of HMD display Distance of HMD display unit to cornea, pupil, retina, fovea (e.g. combiner to cornea, pupil, retina, fovea; waveguide to cornea, pupil, retina, fovea; mirror to cornea, pupil, retina, fovea; OLED display to cornea, pupil, retina, fovea; LED display to cornea, pupil, retina, fovea; HMD display unit to cornea, pupil, retina, fovea; optical elements of HMD display unit to cornea, pupil, retina, fovea; last optical element of HMD display unit to cornea, pupil, retina, fovea Angle of HMD display unit to cornea, pupil, retina, fovea (e.g. combiner to cornea, pupil, retina, fovea; waveguide to cornea, pupil, retina, fovea; mirror to cornea, pupil, retina, fovea; OLED display to cornea, pupil, retina, fovea; LED display to cornea, pupil, retina, fovea; HMD display unit to cornea, pupil, retina, fovea; optical elements of HMD display unit to cornea, pupil, retina, fovea; last optical element of HMD display unit to cornea, pupil, retina, fovea, e.g. when looking straight, e.g. for a given head position Angle of optical axis of HMD, HMD display unit, combiner, waveguide, mirror, OLED display, LED display, optical elements of HMD display unit, last optical element of HMD display unit, optical element(s) of HMD in relationship to cornea, pupil, retina, fovea, e.g. when looking straight Angle of HMD, HMD display unit, combiner, waveguide, mirror, OLED display, LED display, optical elements of HMD display unit, last optical element of HMD display unit, optical element(s) of HMD in relationship to optical axis and/or visual axis of eye, e.g. when looking straight, e.g. for a given head position Height/position/orientation of HMD, HMD display unit, combiner, waveguide, mirror, OLED display, LED display, optical elements of HMD display unit, last optical element of HMD display unit, optical element(s) of HMD in relationship to pupil, cornea, retina, fovea, e.g. how many mm superior or inferior to cornea, pupil, retina, fovea.

In some embodiments, the system comprises a headlight. The headlight can be attached to a head mount, e.g. in a non-limiting, exemplary fashion a head mount 210 (FIGS. 2A-2F), a head band, e.g. head band attached or mounted head light, or attached or mounted to a head mounted display (HMD) or to a surgical loupe. The attachment can comprise one or more locking mechanisms, locking screws and the like. The attachment can be configured to be adjustable, e.g. mounting the headlight at different positions, angles, orientations relative to an HMD and/or the front surface of a user's cornea(s) and/or a surgical loupe. The headlight can be battery powered, e.g. via an integrated battery or a cable connected to a battery, for example in an HMD or attached to the surgeon's waist belt. The headlight can be mounted between the left eye lens apparatus and the right eye lens apparatus of a surgical loupe, with near co-axial or co-axial alignment relative to the optical axis of the surgical loupe. The headlight can be mounted in a non-coaxial alignment relative to the surgical loupe. The headlight can comprise the same or similar attachment mechanisms as a surgical loupe and/or an HMD. The attachment mechanism can provide for swivel, hinge, sliding or other mechanisms configured to allow for moving the headlight into different positions and/or orientations, e.g. a first position and orientation directed towards the target anatomy of a patient and a second position and orientation directed away from the field of view of an HMD and/or a surgical loupe.

Each parameter and/or adjustment can be customized for each individual user. Each parameter and/or adjustment can be individually adjusted. Each parameter related to loupes can be adjusted taking into account one or more parameters related to HMD displays, each parameter related to HMD displays can be adjusted taking into account one or more parameters related to loupes, each parameter related to loupes and each parameter related to HMDs can be adjusted taking into account one or more parameters related to the user's eyes or a combination thereof, all in relationship to the user's facial features, facial shape, interpupillary distance, pupil location, gaze direction, optical axis of the eye(s), visual axis of the eye(s), head position, head orientation or a combination thereof.

In some embodiments, an HMD 200 can be attached to a head mount 210 (FIGS. 2A-2F) or a head band that can comprise multiple adjustment means for positioning and orienting the HMD in relationship to the user's eyes and/or pupil, cornea, retina, fovea, e.g. the optical axis of the eye(s), the visual axis of the eye(s), the pupil, the cornea, the retina, the fovea.

Positioning of an HMD assembly: To limit neck fatigue during a surgical procedure, it can be important to place an HMD assembly in an optimum angular position relative to the profile of the user's face. To achieve this, attachments that connect the HMD to the head mount can have intermediate components to allow for adjustment. Such components can be, for example, but not limited to:

A first component 275 rotationally fixed to the head mount with optional serrations 270 to allow for rotational adjustment.

A second component having mating serrations to provide a fixed adjusted position and a mechanical adjustment mechanism 260 for the $3^{rd}$ component to rest against. This component can be rotationally adjusted to provide a desired HMD position and/or orientation for a surgeon. A pin can be used to stop 285 the HMD, e.g. to rest in when the assembly is flipped up or down, e.g. to the desired down position for looking at/through the HMD, or the desired up position, when a view at/through the HMD is not desired.

A $3^{rd}$ component holding the HMD and having an optional stop mechanism 285, e.g. comprising at least one pin, that can abut the stop and/or the dwell of a second component.

A $4^{th}$ component such as a tightening knob 280 that can fix the assembly in an adjusted position desired by a user, e.g. a position where no or only small parts of the HMD visual field are cut off, or where all parts of the HMD visual field are visible.

Other mechanisms, including, but not limited to, Velcro, hinges, straps, magnets, can be used for placing the HMD in relationship to a head mount or head band worn by the user; the HMD can optionally be moved into multiple positions in relationship to the user's eye and/or head mount or head band.

In some embodiments, the loupes are integrated with the HMD. In some embodiments, the loupes are front lens mounted with the HMD. For example, an HMD can comprise a front lens, e.g. diffracting or non-diffracting (e.g. for vision correction), into which the loupe can be integrated. The front lens can also be part of a combiner. The loupe can be integrated and front mounted with the front lens (front mounted with lens, "FML"), including a front lens that is part of the combiner. The front lens is the portion of the HMD that is facing away from the user's eye(s).

In some embodiments, the loupes are through the lens ("TTL"), i.e. with the loupe extending through an HMD, e.g. a lens portion of an HMD or other portion of an HMD. The lens portion or other portion can comprise at least part of the HMD display unit, including a combiner, a mirror, an LED, an OLED.

In some embodiments, the system comprises a loupe attached to a head mount, a head band, and/or an HMD. In some embodiments, the loupe is not integrated into the HMD, but separate from the HMD. In some embodiments, the loupe is not integrated into the HMD, but separate from the HMD and, optionally, connected to the HMD and/or a head mount, head band or combination thereof, for example via an attachment mechanism. In some embodiments, the HMD and the loupes have separate housings. In some embodiments, the HMD and the loupes have separate housings, optionally connected via an attachment mechanism. In some embodiments, the housing of an HMD and the housing of a loupe can be connected to a head mount, a head band, each other, or a combination thereof, e.g. via an attachment mechanism, as described in the specification. The attachment mechanism can be adjustable, e.g. for an individual user including the facial shape, eye position, interpupillary distance etc.

In some embodiments, the position and/or orientation of an HMD, HMD display unit and/or combiner is adjusted in relationship to a user's facial shape, eye position, interpupillary distance and/or skull shape. Once the adjustment has been performed, the position and/or orientation of an HMD, HMD display unit and/or combiner can be fixated and/or maintained in relationship to a user's facial shape, eye position, interpupillary distance, eyes and/or skull. In some embodiments, the position and/or orientation of surgical loupe is adjusted in relationship to a user's facial shape, eye position, interpupillary distance and/or skull shape and/or HMD position and/or orientation. Once the adjustment has been performed, the position and/or orientation of the surgical loupe can be fixated and/or maintained in relationship to the user's facial shape, eye position, interpupillary distance, eyes and/or skull and/or HMD position and/or orientation. Optionally, the loupes can be attached to an attachment mechanism that can support moving the loupes into a position outside the visual field of the user, and moving them back, e.g. "flipping up" and "flipping back". Thus, in some embodiments, the HMD, HMD display unit and/or combiner and the surgical loupes are fixated during use with respect to a user's facial shape, eye position, interpupillary distance, eyes and/or skull. In some embodiments, the HMD, HMD display unit and/or combiner are fixated during use with respect to a user's facial shape, eye position, interpupillary distance, eyes and/or skull, while the loupes can optionally be moved from a see through position, e.g. in front of and/or below the HMD, HMD display unit or combiner, to a second position outside the visual field of the user, e.g. a "flipped up" position.

In some embodiments, the HMD and the surgical loupes are connected to each other and move in relationship to each other. In some embodiments, the surgical loupes are not directly coupled to the HMD (but, for example, attached to a head mount or head band) and HMD and/or surgical loupes are configured to be adjusted and/or move independent of each other.

In some embodiments, the system comprises adjustment means for positioning and orienting the loupe in relationship to the user's eyes and/or pupils, e.g. the optical axis of the eye(s), the visual axis of the eye(s), the pupil, the cornea, the retina, the fovea e.g. for viewing an anatomic structure such as a knee, a hip, a spine, an organ, a heart, a brain) of a patient with a magnified view. Referring to FIGS. 3A-3K, a loupe 320 can be attached to a head mount and/or an HMD 300 that can comprise multiple adjustment means for positioning and orienting the loupe 320 in relationship to the user's eyes and/or pupils 330, e.g. the optical axis of the eye(s), the visual axis of the eye(s), the pupil, the cornea, the retina, the fovea e.g. for viewing an anatomic structure 340 (e.g. a knee, a hip, a spine, an organ, a heart, a brain) of a patient 350 with a magnified view. In some embodiments, a loupe is attached to an HMD 300 that can comprise multiple adjustment means for positioning and orienting the loupe in relationship to the user's eyes and/or pupils, e.g. the optical axis of the eye(s), the visual axis of the eye(s), the pupil, the cornea, the retina, the fovea.

In some embodiments, a loupe 320 is attached to an HMD 300 that can comprise multiple adjustment means for positioning and orienting the loupe in relationship to the HMD, e.g. for orienting the optical axis of the loupe with the optical axis of the HMD and/or the optical and/or visual axis of the eye.

Figure 3A:
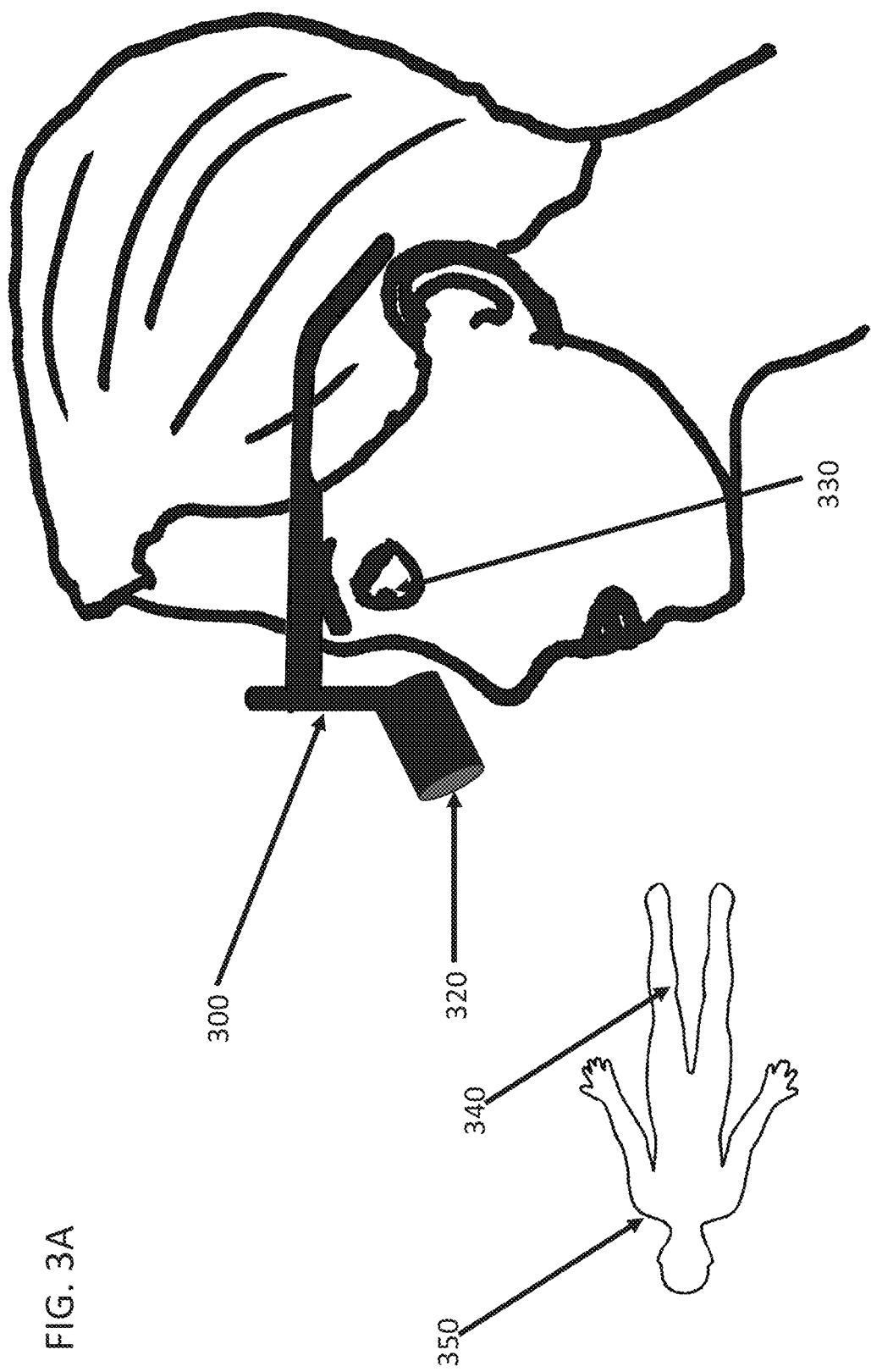
FIG. 3A illustrates an HMD used in conjunction with a surgical loupe, with a surgeon observing an anatomic structure through the HMD and/or the surgical loupe, according to various embodiments.
Figure 3B:
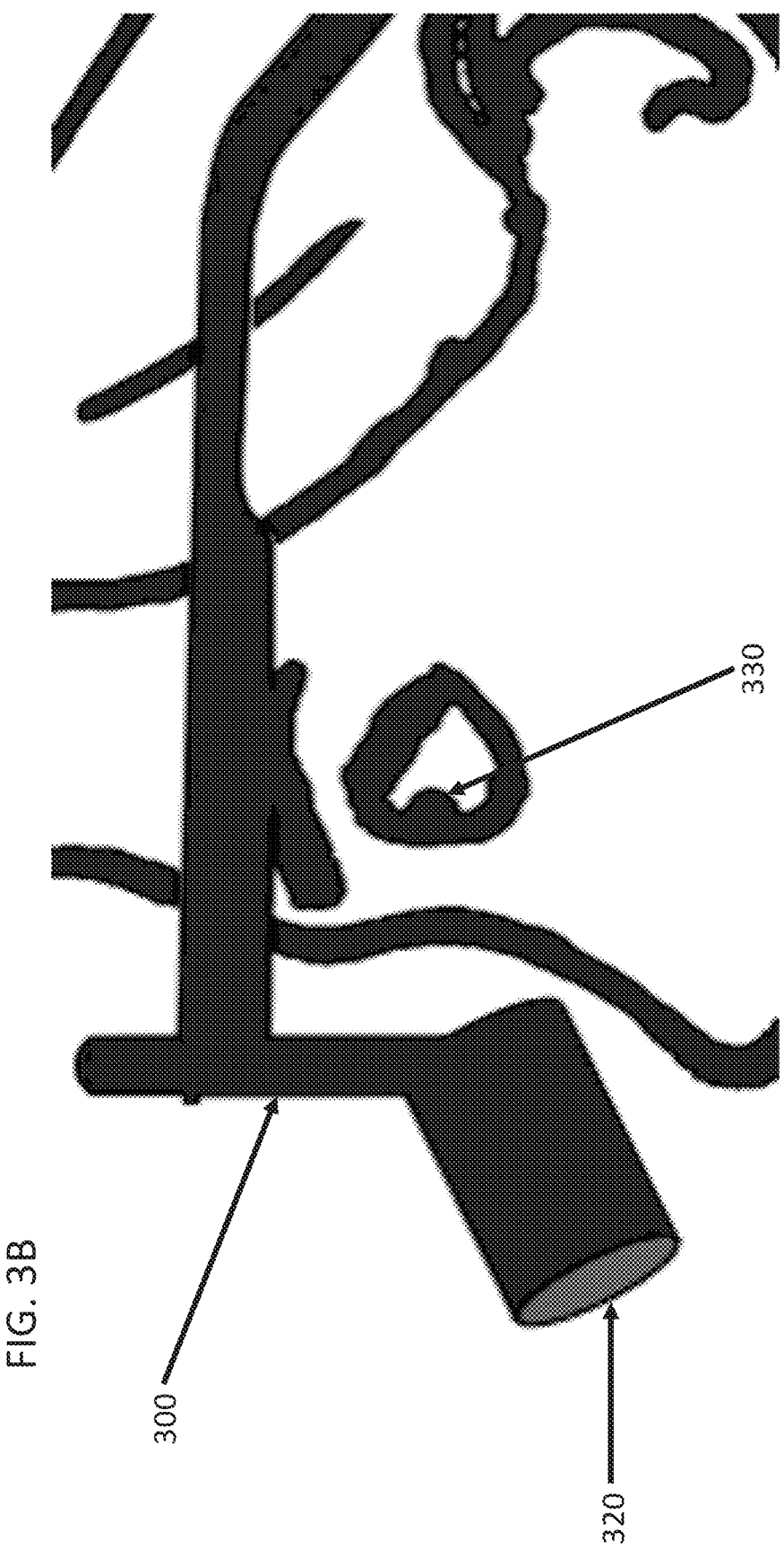
FIG. 3B is a magnified view of FIG. 3A.
Figure 3C:
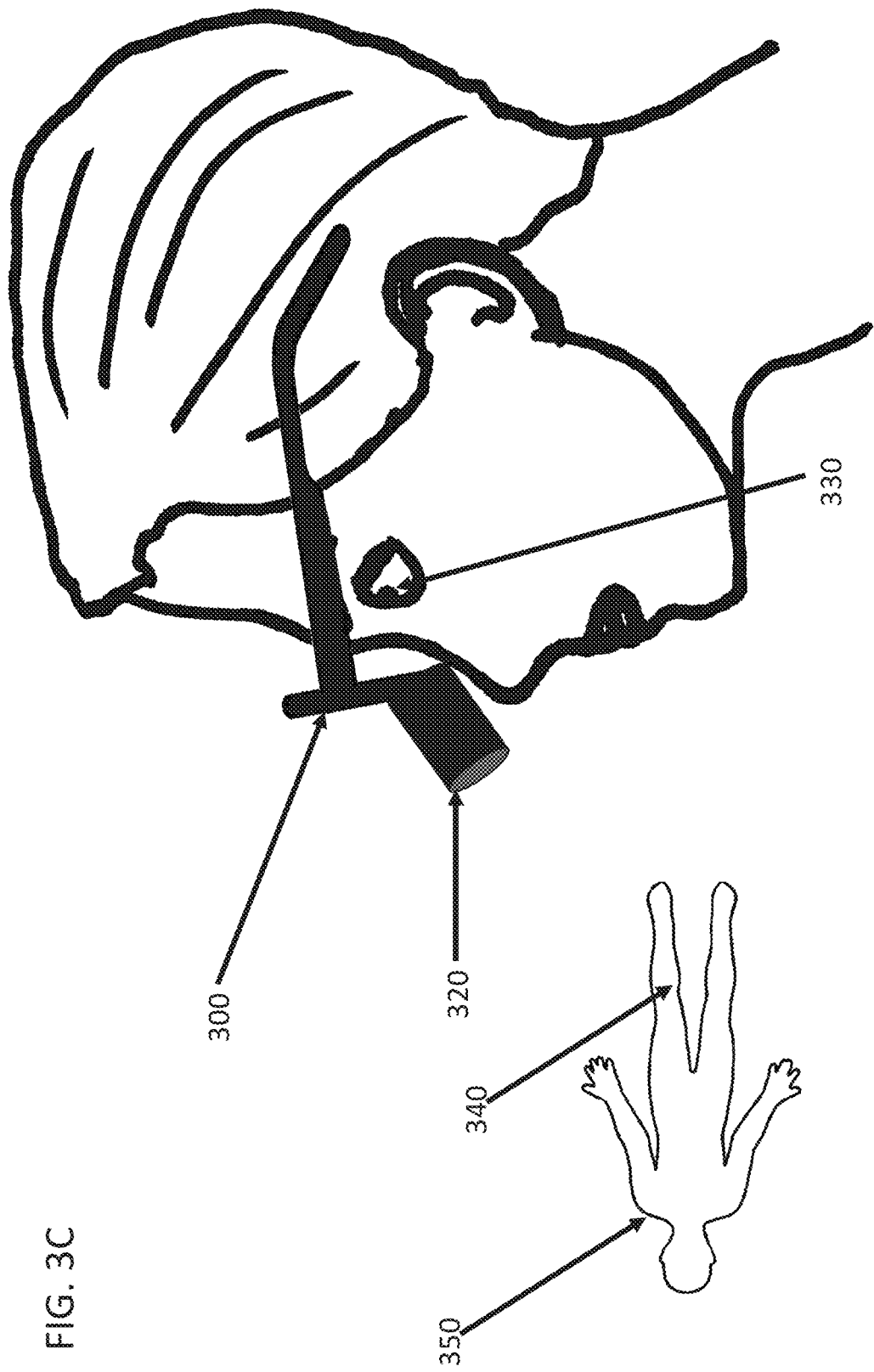
FIG. 3C and FIG. 3D illustrate an HMD used in conjunction with a surgical loupe, with the HMD shown in different positions relative to the user's eye, according to various embodiments.
Figure 3D:
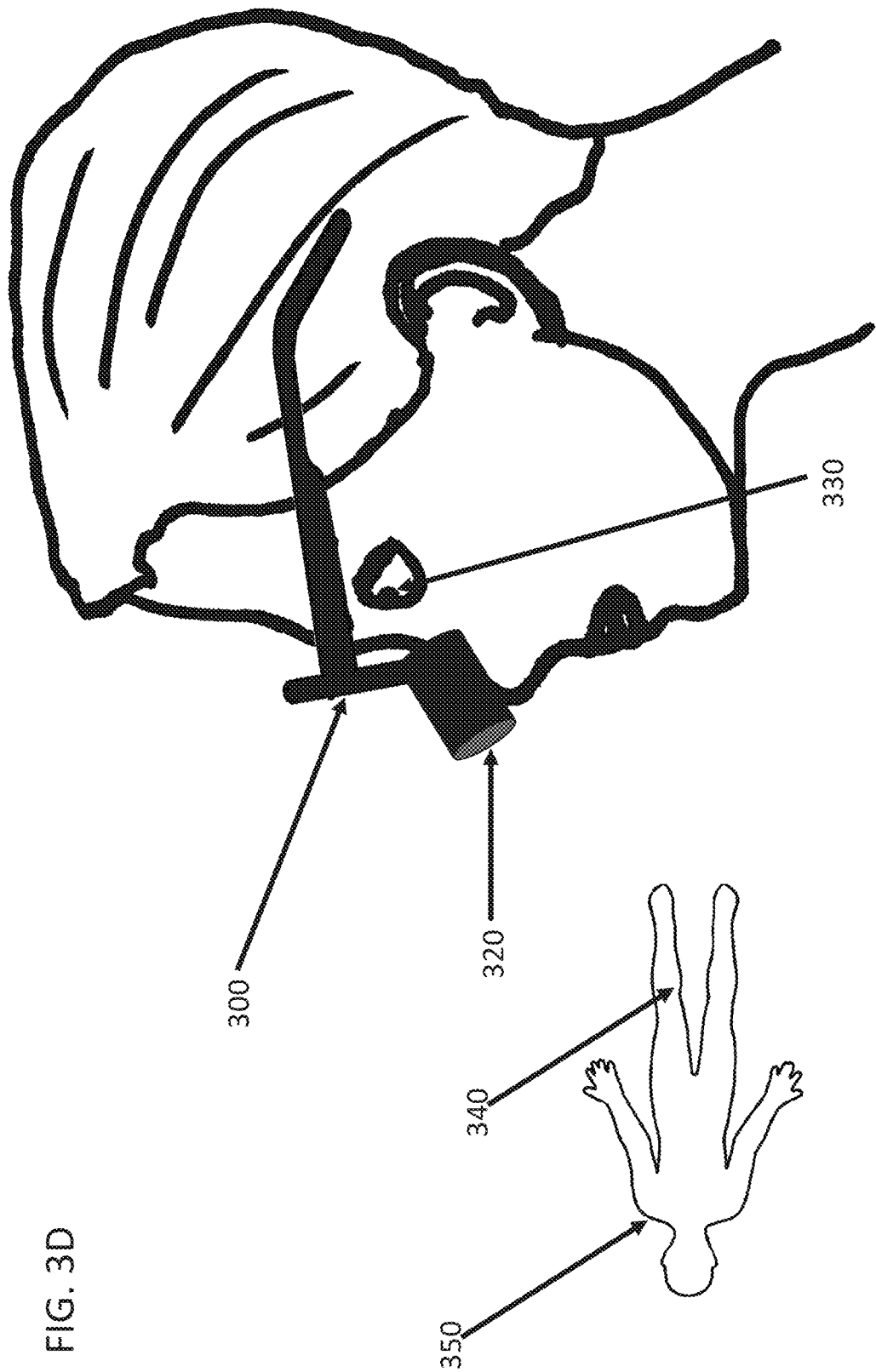

Once a user has identified an optimal HMD 300 position and/or orientation (with exemplary, non-limiting positions and/or orientations shown in FIGS. 3A, 3C, and 3D, for example), that position and/or orientation can be secured or stored, for example using mechanical adjustment means. A user can then optionally revisit or re-use the secured or stored HMD position.

Figure 3E:
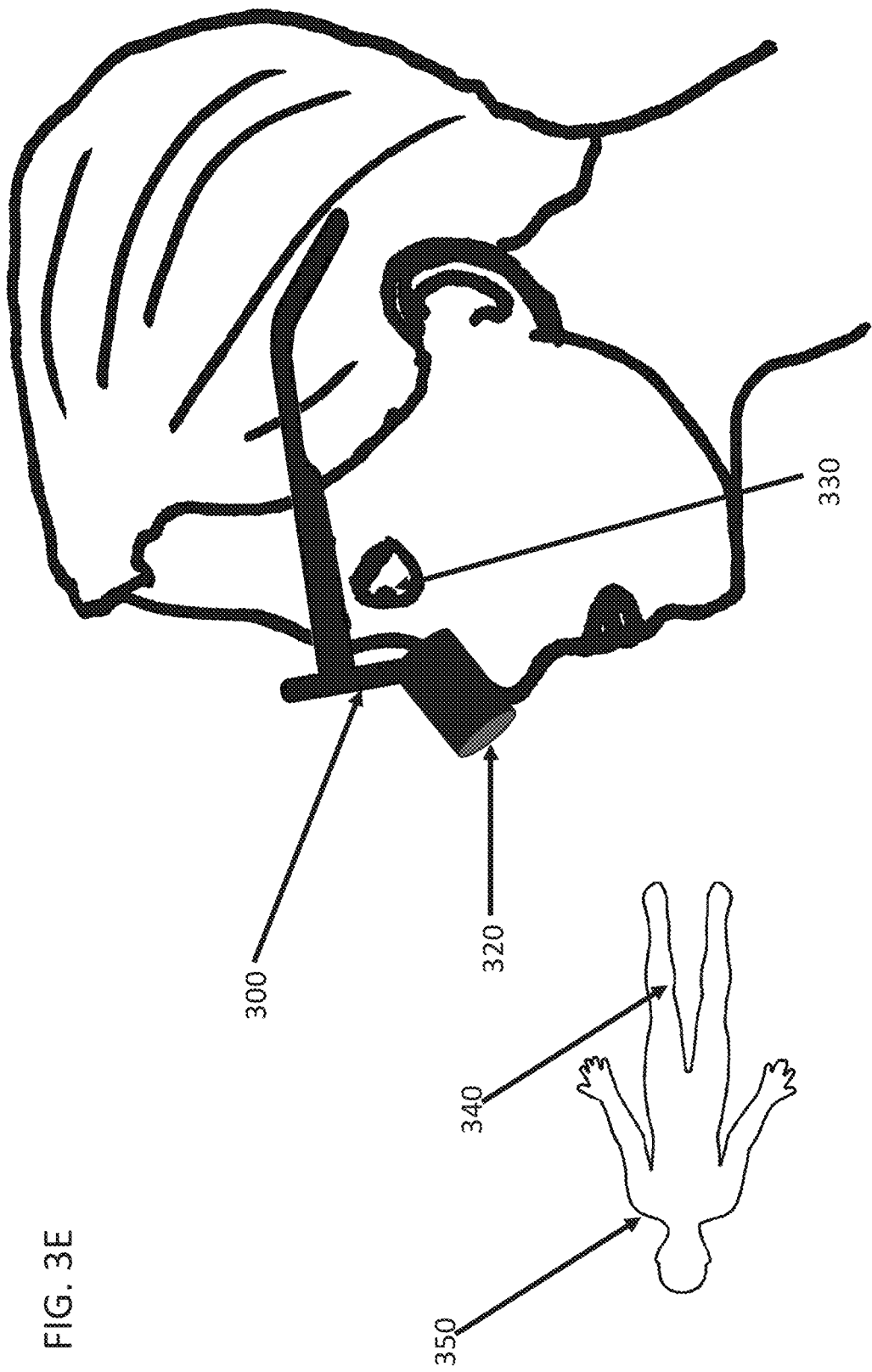
FIG. 3E illustrates an HMD used in conjunction with a surgical loupe, with the surgical loupe shown in a different position relative to the user's eye compared to FIG. 3D according to various embodiments.
Figure 3F:
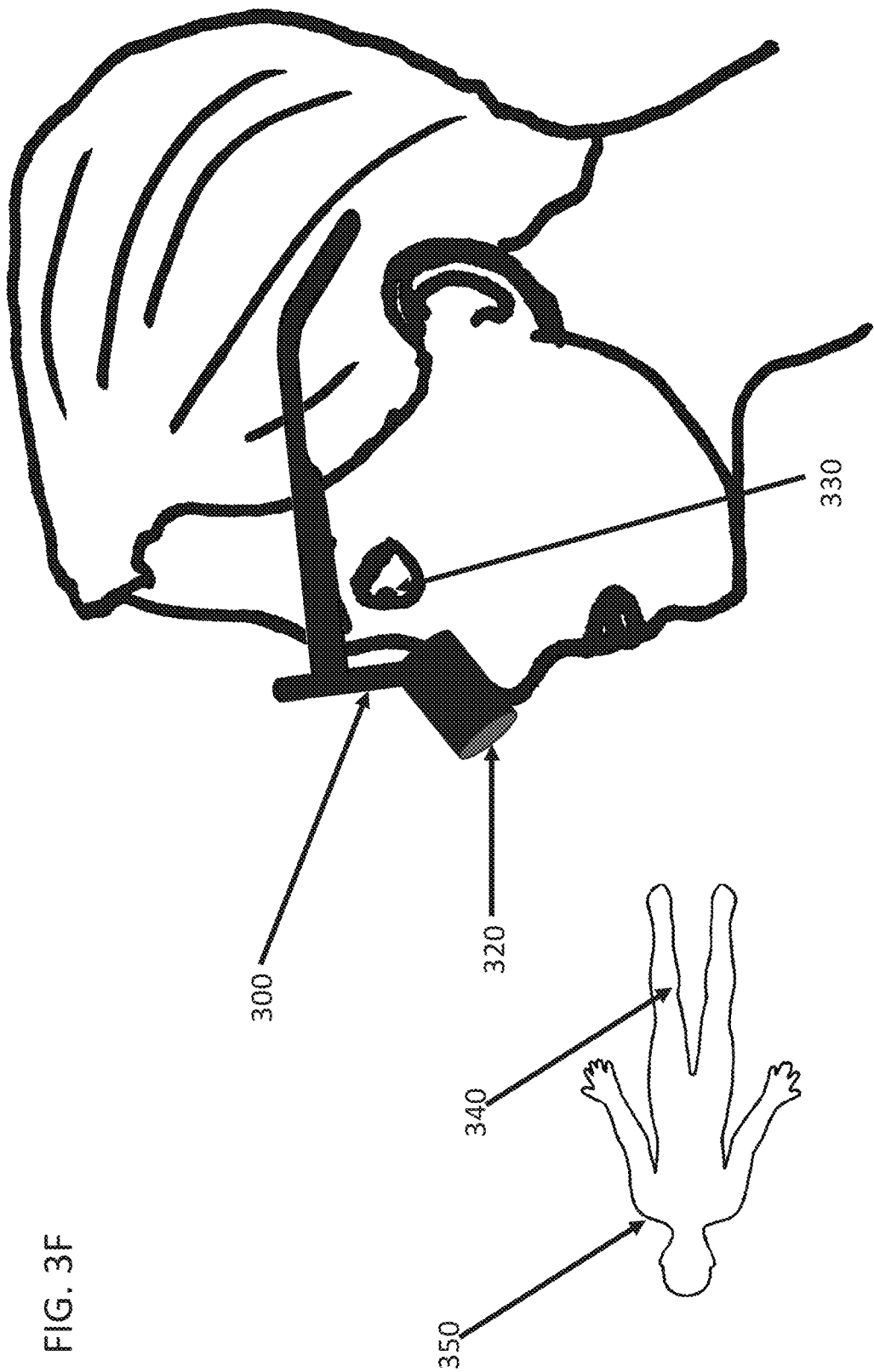
FIG. 3F illustrates an HMD used in conjunction with a surgical loupe, with the HMD shown in a different positions relative to the user's eye compared to FIG. 3E according to various embodiments.
Figure 3G:
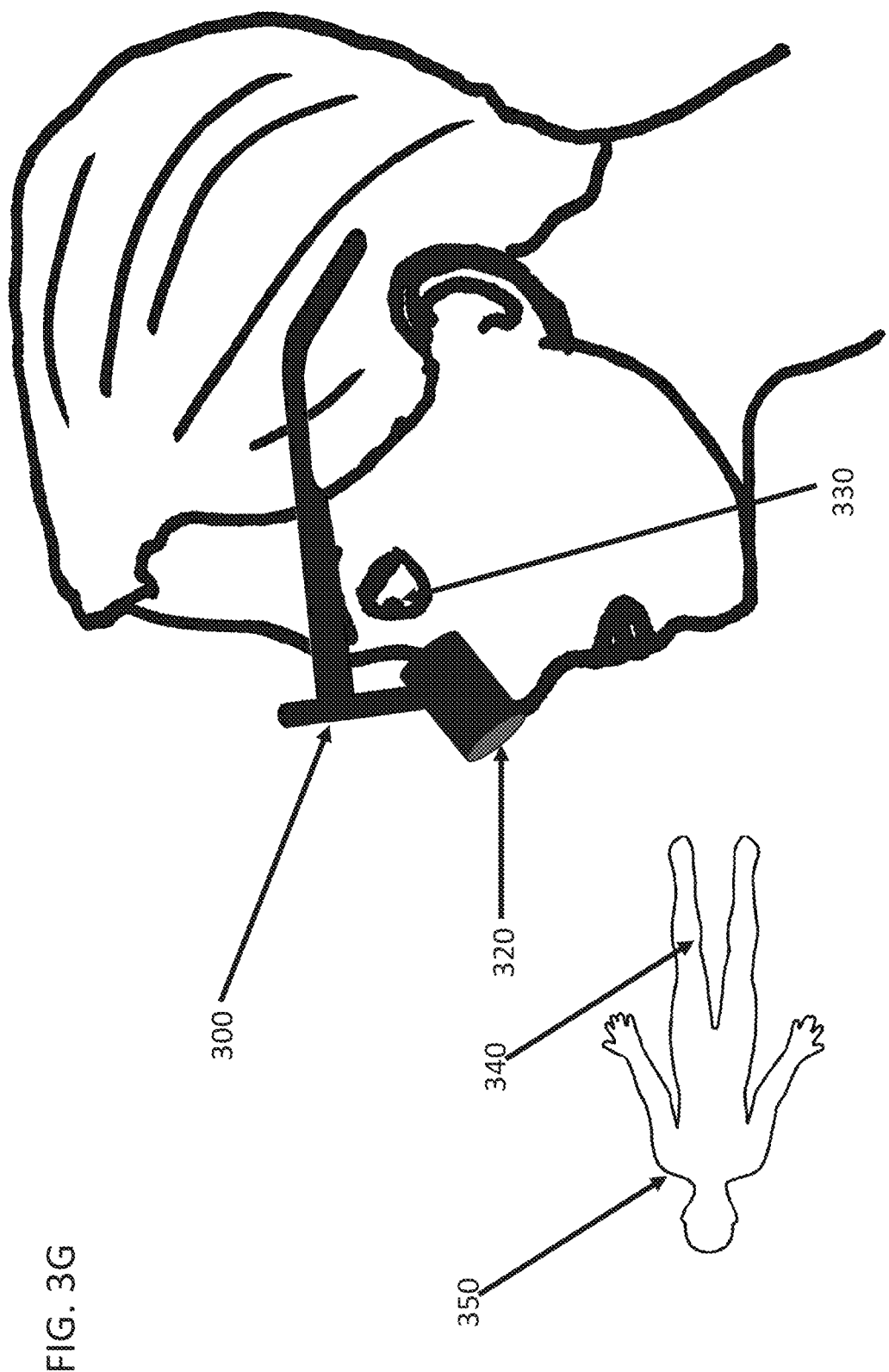
Figure 3H:
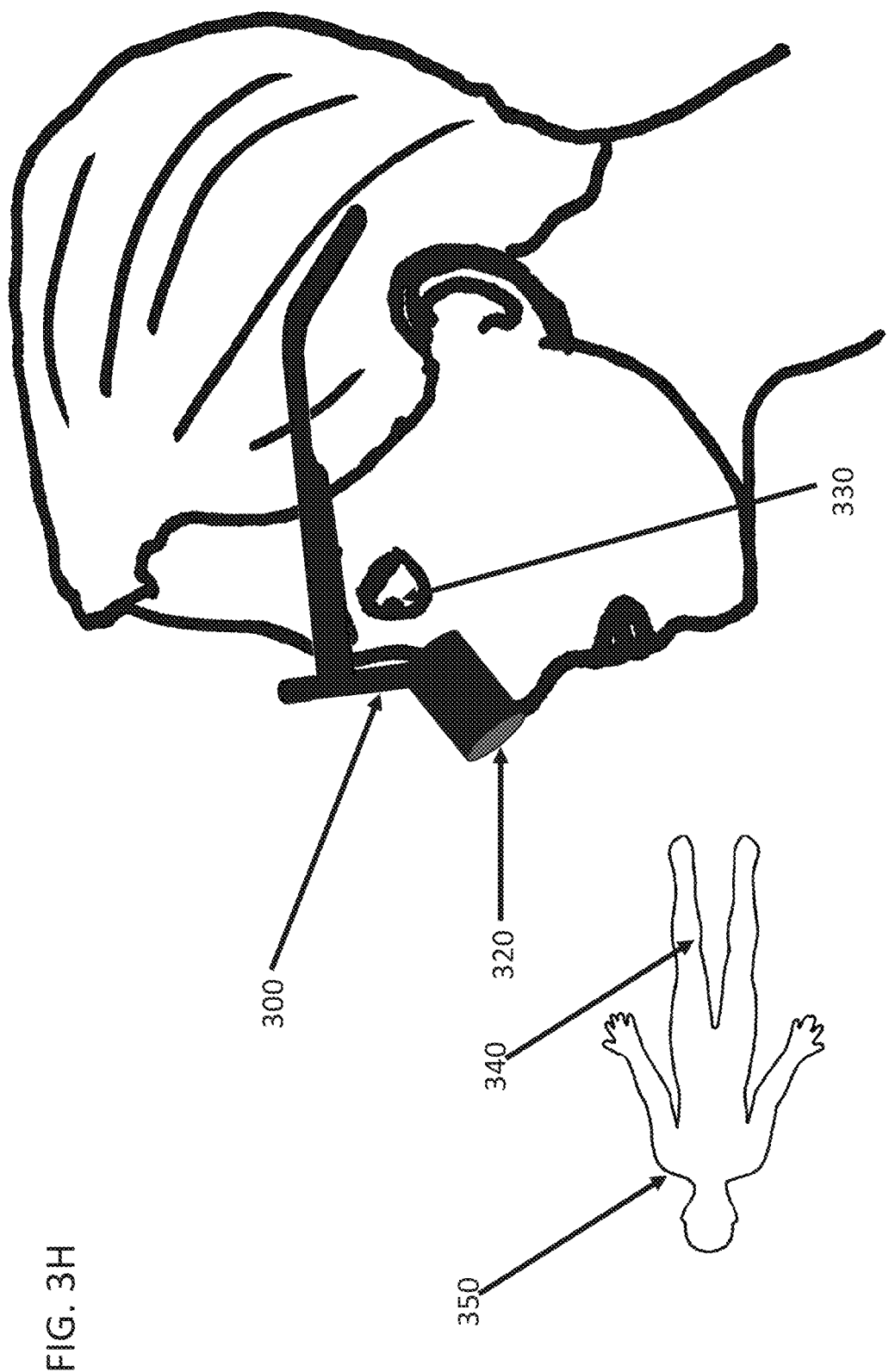
Figure 31:
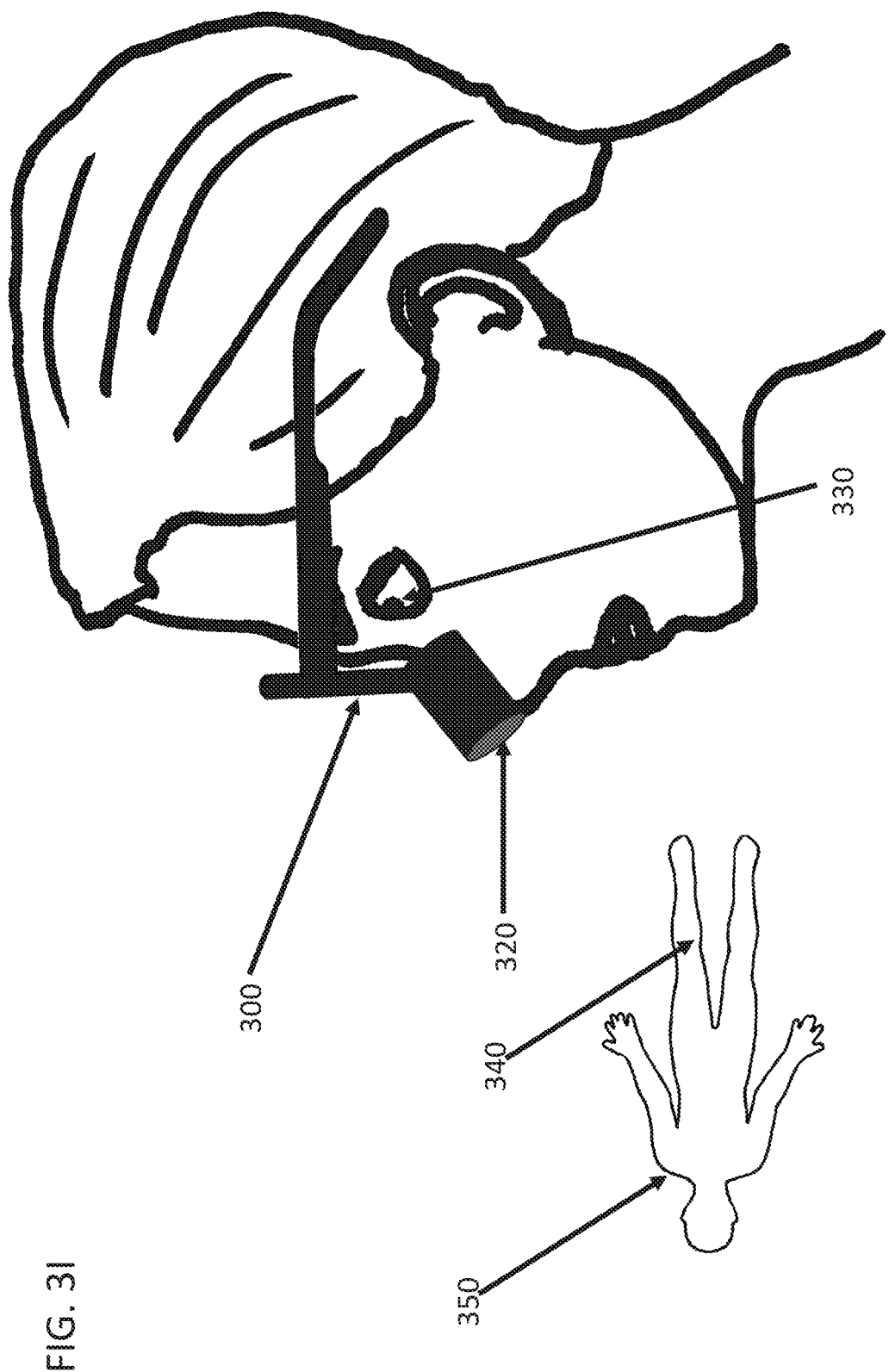

Once a user has identified an optimal loupe 320 position and/or orientation (with exemplary, non-limiting positions and/or orientations shown in FIGS. 3D and 3E, for example), that position can be secured or stored, for example using mechanical adjustment means. A user can then optionally revisit or re-use the secured or stored HMD position.

Figure 2A:
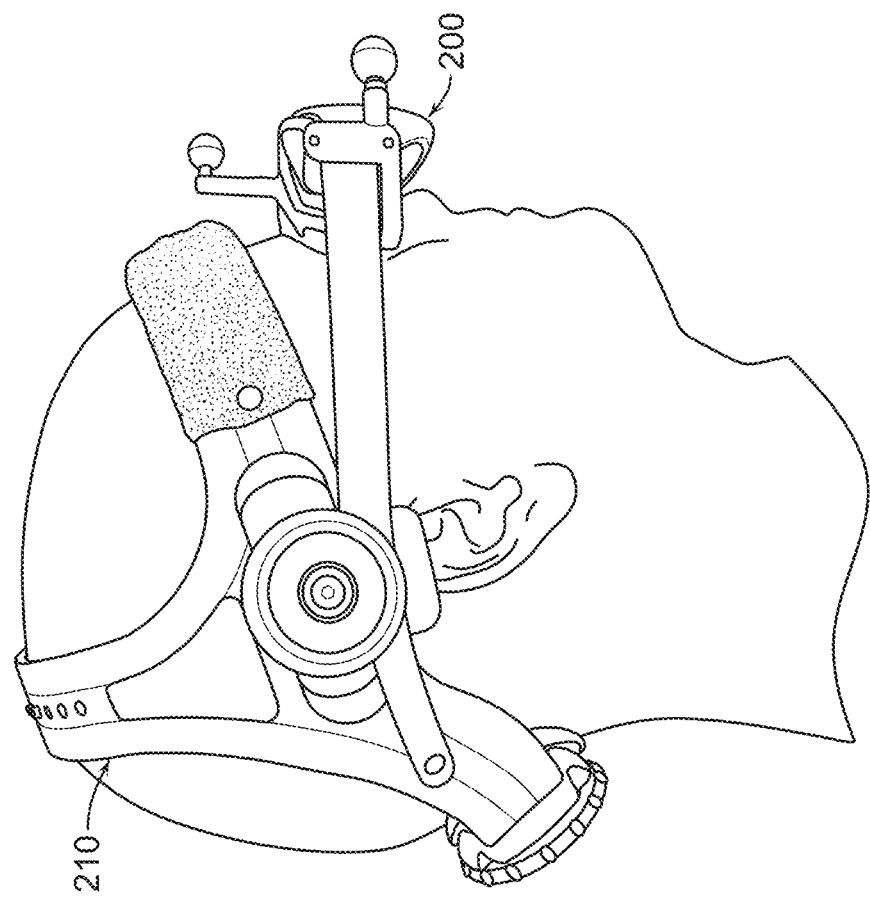
FIG. 2A illustrates a side view of an HMD attached to a head mount according to various embodiments.
Figure 2B:
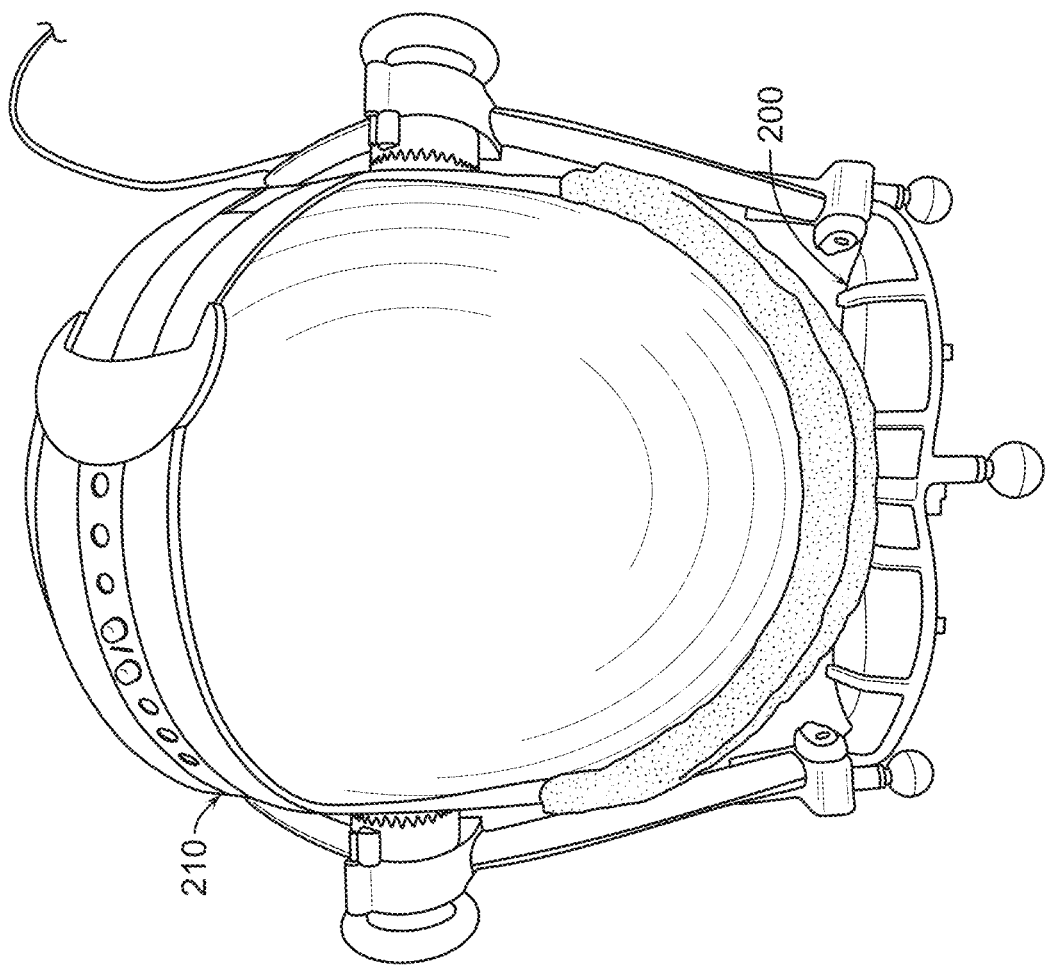
FIG. 2B illustrates a top view of an HMD attached to a head mount according to various embodiments.
Figure 2C:
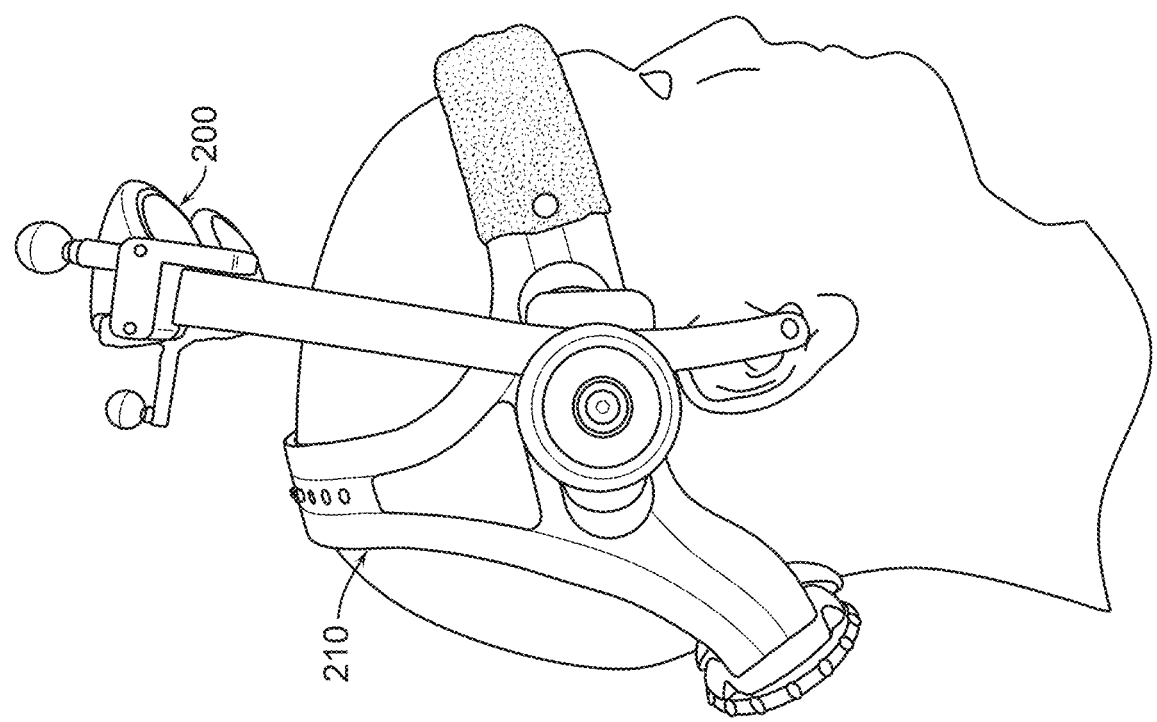
FIG. 2C illustrates a side view of an HMD attached to a head mount, with the HMD flipped up, outside the visual field of the user according to various embodiments.
Figure 2D:
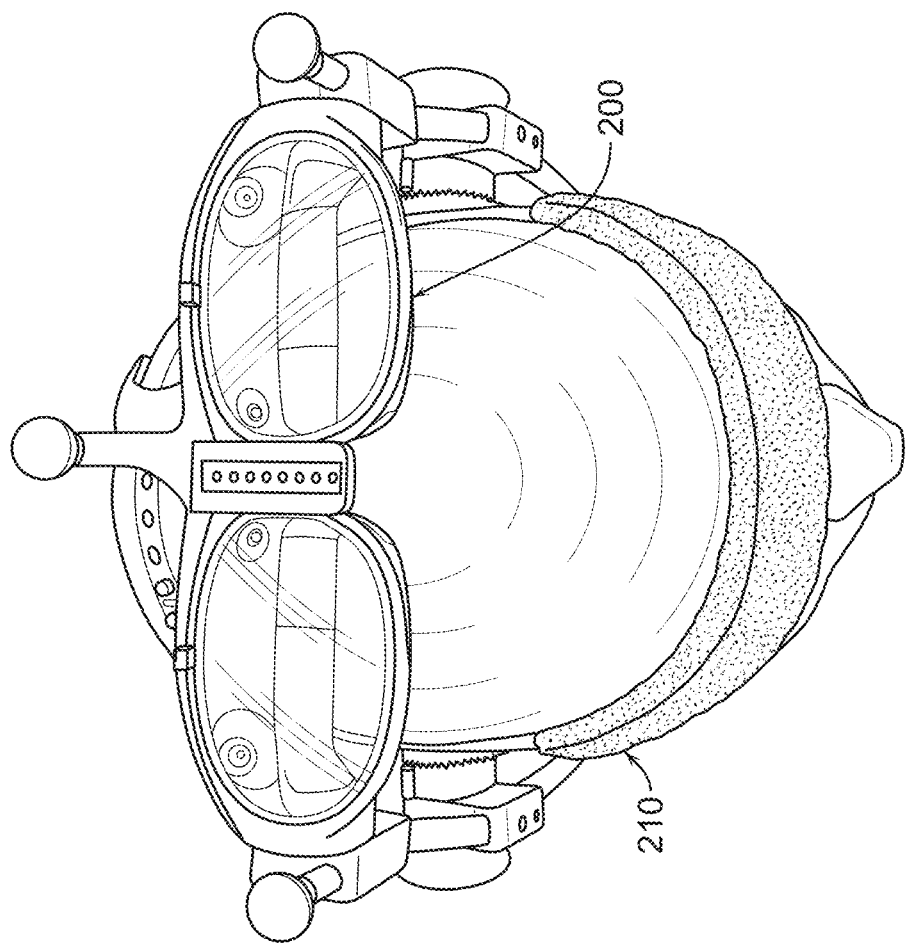
FIG. 2D illustrates a top view of an HMD attached to a head mount, with the HMD flipped up, outside the visual field of the user, according to various embodiments.
Figure 2E:
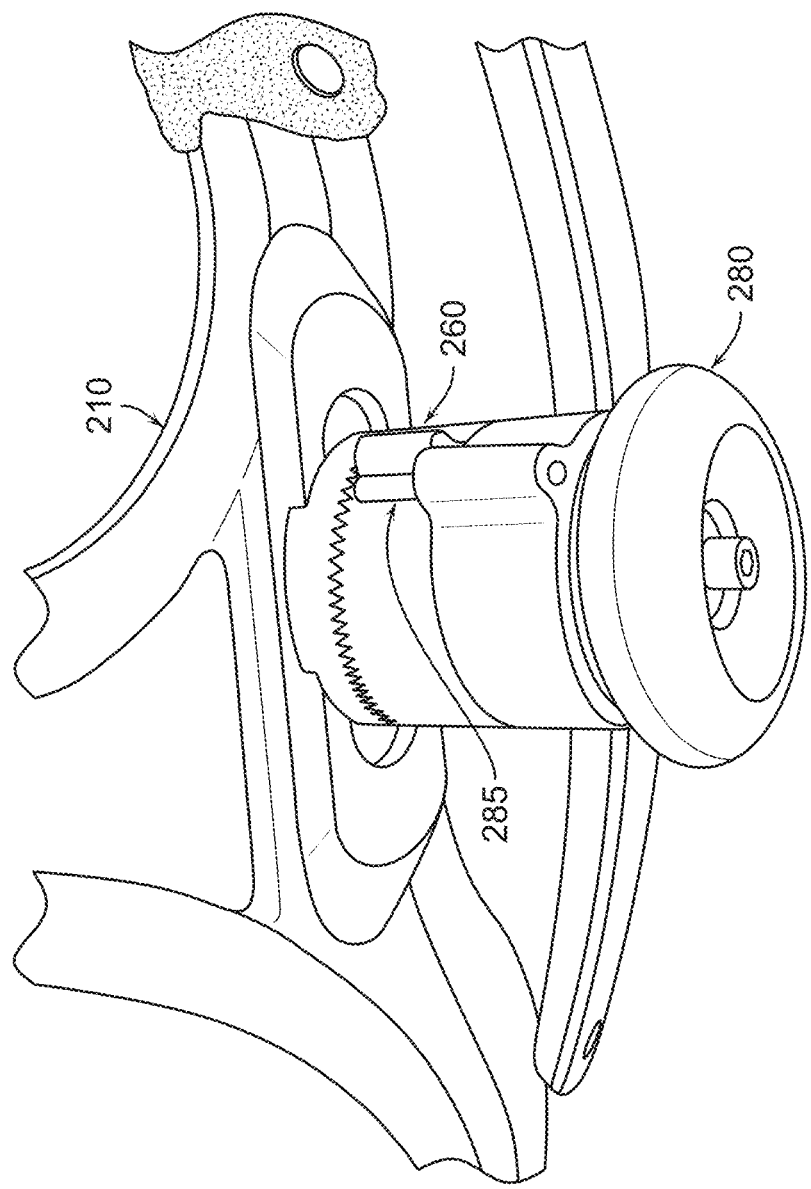
FIG. 2E and FIG. 2F illustrate a side attachment and adjustment mechanism of the HMD to the head mount, for example with a mechanical stop for different positions, according to various embodiments.
Figure 2F:
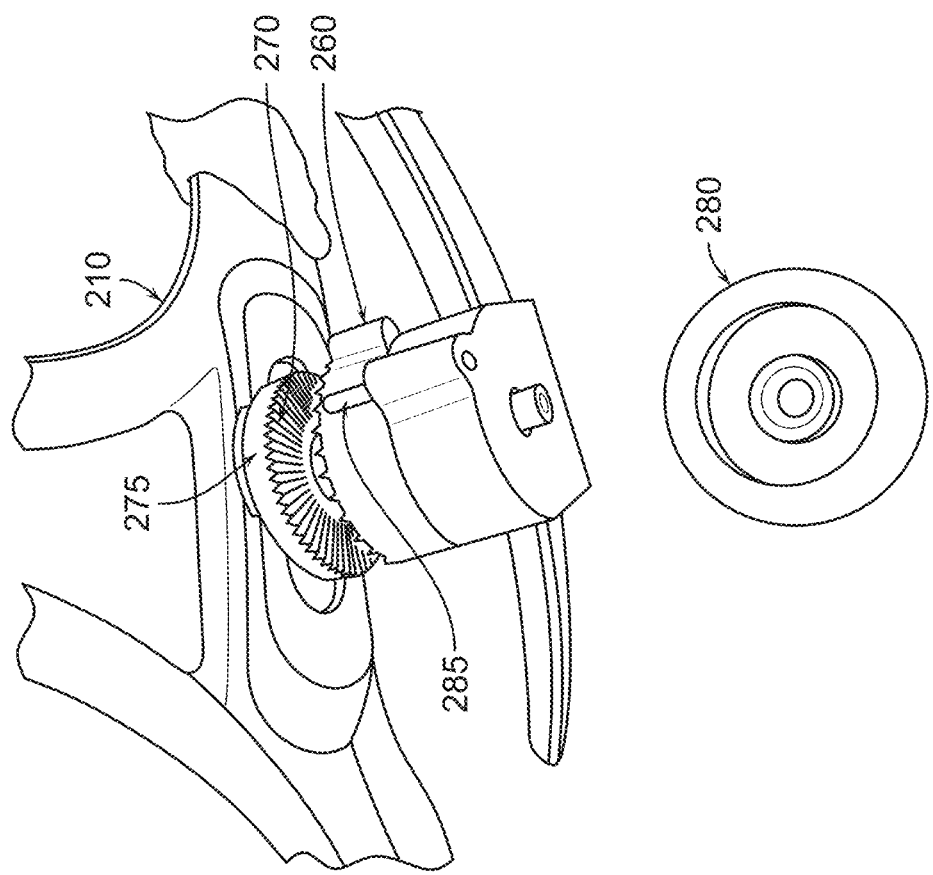

In some embodiments, the HMD comprises a mechanical adjustment mechanism. In some embodiments, the adjustment mechanism optionally includes a textured surface or a surface with one or more surface features, such as ridges and valleys, for securing or locking the HMD in a defined position in relationship to a head mount and/or a user's face and/or eye(s). In some embodiments, the defined position is a predetermined position in relationship to a head mount and/or a user's face and/or eye(s). The HMD can be adjusted, e.g. up or down or forward or backward in relationship to the user's eye(s), an optical and/or visual axis of the eye, a cornea, a pupil, a retina, a fovea. In some embodiments, once the HMD is adjusted, the HMD is locked in relationship to the head mount and/or a user's face and/or eye(s) by tightening one or more knobs for tightening the space between a first and, optionally, a second textured surface. The HMD can optionally compromise a second mechanical adjustment mechanism that is configured to move the HMD superior and/or inferior in relationship to a head mount. Referring to FIGS. 2E-2F, an HMD can comprise a mechanical adjustment mechanism 260 that can, optionally, include a textured surface or a surface with one or more surface features 270, e.g. ridges and valleys, for example for securing or locking the HMD in a defined, optionally predetermined position, in relationship to a head mount and/or a user's face and/or eye(s). The HMD can be adjusted, e.g. up or down or forward or backward in relationship to the user's eye(s), e.g. an optical and/or visual axis of the eye, a cornea, a pupil, a retina, a fovea and the HMD can then be locked in relationship to the head mount and/or a user's face and/or eye(s) by tightening one or more knobs 280 for tightening the space between a first and, optionally, a second textured surface. The HMD can optionally comprise a second mechanical adjustment mechanism that is configured to move the HMD superior and/or inferior in relationship to a head mount.

In some embodiments, the mechanical adjustment mechanism 260 is configured to secure or lock the HMD 200 in a first, e.g. down, position (FIGS. 2A and 2B) using a stop 285 locking or securing it into a defined position relative to the user's eye(s), pupil, cornea, retina, fovea, vertex distance, visual axis of the eye, optical axis of the eye or a combination thereof. The HMD 200 can then optionally be moved or flipped up into a second, e.g. superior position (FIGS. 2C, 2D), optionally with a second stop mechanism. The mechanical adjustment mechanism and the optional stop mechanism 285 can be configured to ensure that the HMD returns to the defined first position relative to the user's eye(s), pupil, cornea, retina, fovea, vertex distance, visual axis of the eye, optical axis of the eye or a combination thereof when the HMD is moved down again to the first position (FIGS. 2A, 2B).

In some embodiments, it is desirable that an HMD position is adjusted in a manner so as to ensure that no parts of the display are cut off. In some embodiments, the HMD display (and/or any parts thereof) position is adjusted in a manner so that no portions of the field of view of the display are cut of or not visible to the user. The adjustment can be an adjustment or modification of the distance (FIGS. 3G, and 3H) and/or angle (FIGS. 3H, and 3I) of the HMD display unit, including, for example, a combiner, to the cornea of the user's eye. In some embodiments, it is desirable that an HMD position is adjusted in a manner so that no clinically relevant parts of the display are cut of or not visible to the user. For example, in spinal surgery, an HMD position can be chosen by a surgeon that ensure that no portion of an axial, sagittal and/or coronal image(s) are cut off when the user looks through the HMD display. In another example, an HMD display can display a reference or calibration frame or markers around the display edge or in multiple areas of near the display edge, or 5%, 10%, or 15% within the display edge and an HMD position can be chosen by a surgeon that ensures that no portion of the display edge is cut off or not included. The HMD position can be adjusted and, optionally, locked or secured relative to the head mount and/or user's eye(s) so that no or only a limited part of the HMD display is cut off when the user looks through the HMD.

Proper positioning of an HMD and loupes for a surgeon is important for visualization of the HMD display and magnified views through the loupe during a surgical procedure. In some exemplary, non-limiting embodiments, a loupe can be attached to an HMD, an HMD frame, an HMD housing, a head mount, a head band, an array attached to the HMD, an array attached to the HMD frame, an array attached to the HMD housing, an array attached to the head mount, or a combination thereof.

In some embodiments, a loupe attachment to an HMD, an HMD frame, an HMD housing, a head mount, a head band, an array attached to the HMD, an array attached to the HMD frame, an array attached to the HMD housing, an array attached to the head mount, or a combination thereof comprises one or more features/mechanisms that are slideably engagable, e.g. a dovetail like feature/mechanism, a rail like feature/mechanism, a rod and piston like feature/mechanism. In some embodiments, a loupe attachment to an HMD, an HMD frame, an HMD housing, a head mount, a head band, an array attached to the HMD, an array attached to the HMD frame, an array attached to the HMD housing, an array attached to the head mount, or a combination thereof comprises one or more features/mechanisms that are rotatably engagable, e.g. a hinge like feature/mechanism, a swivel like feature/mechanism, or any other rotation accommodating feature/mechanism.

In some embodiments, a loupe attachment to an HMD, an HMD frame, an HMD housing, a head mount, a head band, an array attached to the HMD, an array attached to the HMD frame, an array attached to the HMD housing, an array attached to the head mount, or a combination thereof comprises one or more features/mechanisms that are rotatably and slideably engagable. In some embodiments, the slideable and/or rotatable feature/mechanism(s) comprise a first, a second, a third or more locking or securing features/mechanisms. For example, a screw can be utilized to lock a slideably engagable mechanism and/or feature at a predetermined and/or defined height, e.g. for locking and/or securing a loupe at the predetermined and/or defined height in relationship to an HMD, an HMD frame, an HMD housing, a head mount, a head band an array attached to the HMD, an array attached to the HMD frame, an array attached to the HMD housing, an array attached to the head mount, or a combination thereof.

In some embodiments, the slideable and/or rotatable feature/mechanism(s) comprise a first, a second, a third or more locking or securing features/mechanisms. For example, a screw, or any other locking or securing mechanism, can be utilized to lock a slideable or rotatable or slideable and rotatable engagable mechanism and/or feature at a predetermined or defined position, orientation, distance, angle, e.g. for locking and/or securing a loupe at a predetermined and/or defined height, distance, orientation, angle in relationship to an HMD, HMD attachment (direct or indirect), HMD display unit, e.g. comprising a combiner, at a predetermined or defined height and/or distance and/or angle relative to the user's eyes/cornea/pupil/retina/fovea, optical axis of the eye(s), visual axis of the eye(s) or a combination thereof.

Figure 3J:
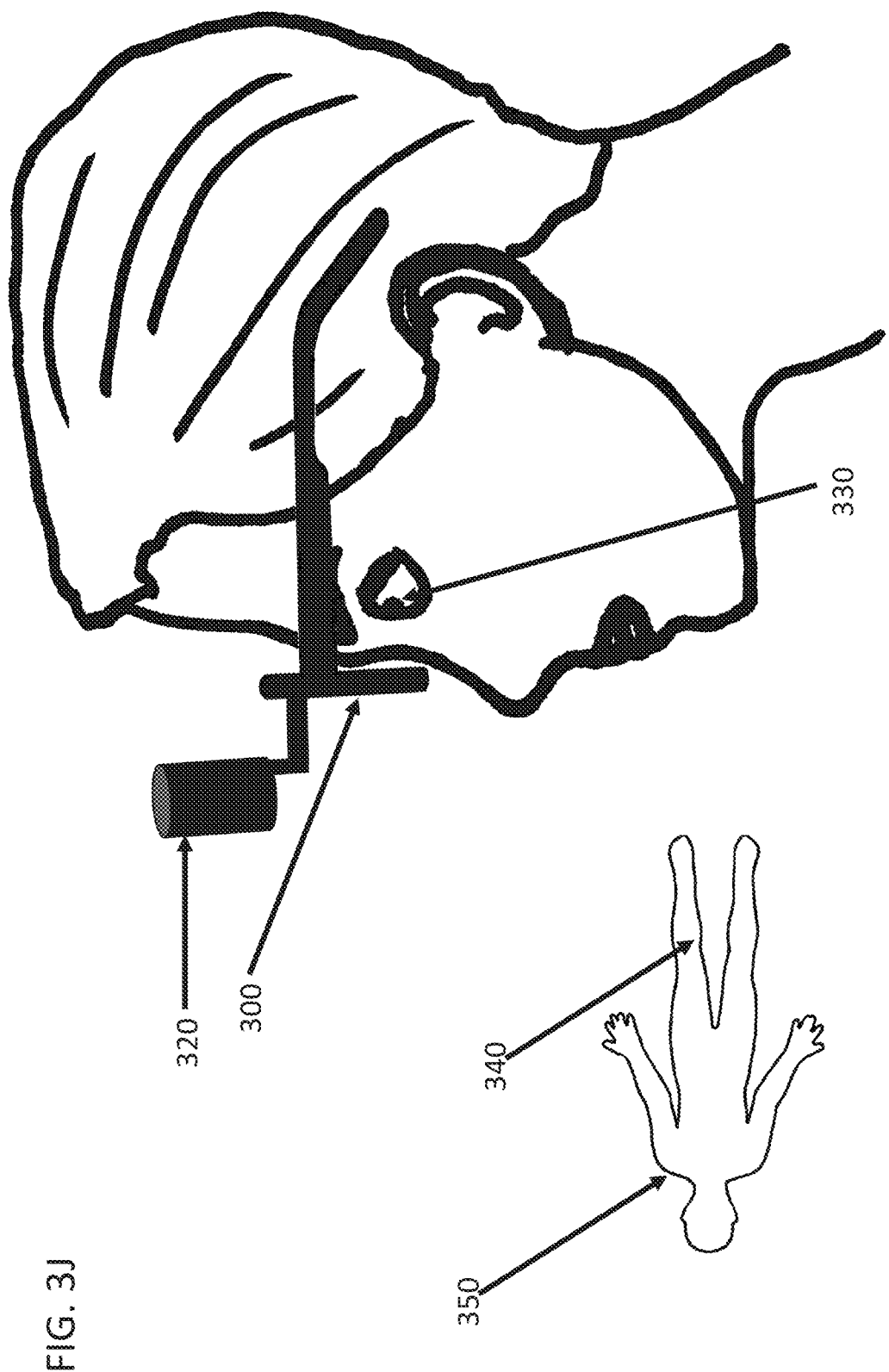
FIG. 3J illustrates an HMD used in conjunction with a surgical loupe, with the surgical loupe shown in a flipped up position relative to the user's eyes, above the visual field of the user, according to various embodiments.
Figure 3K:
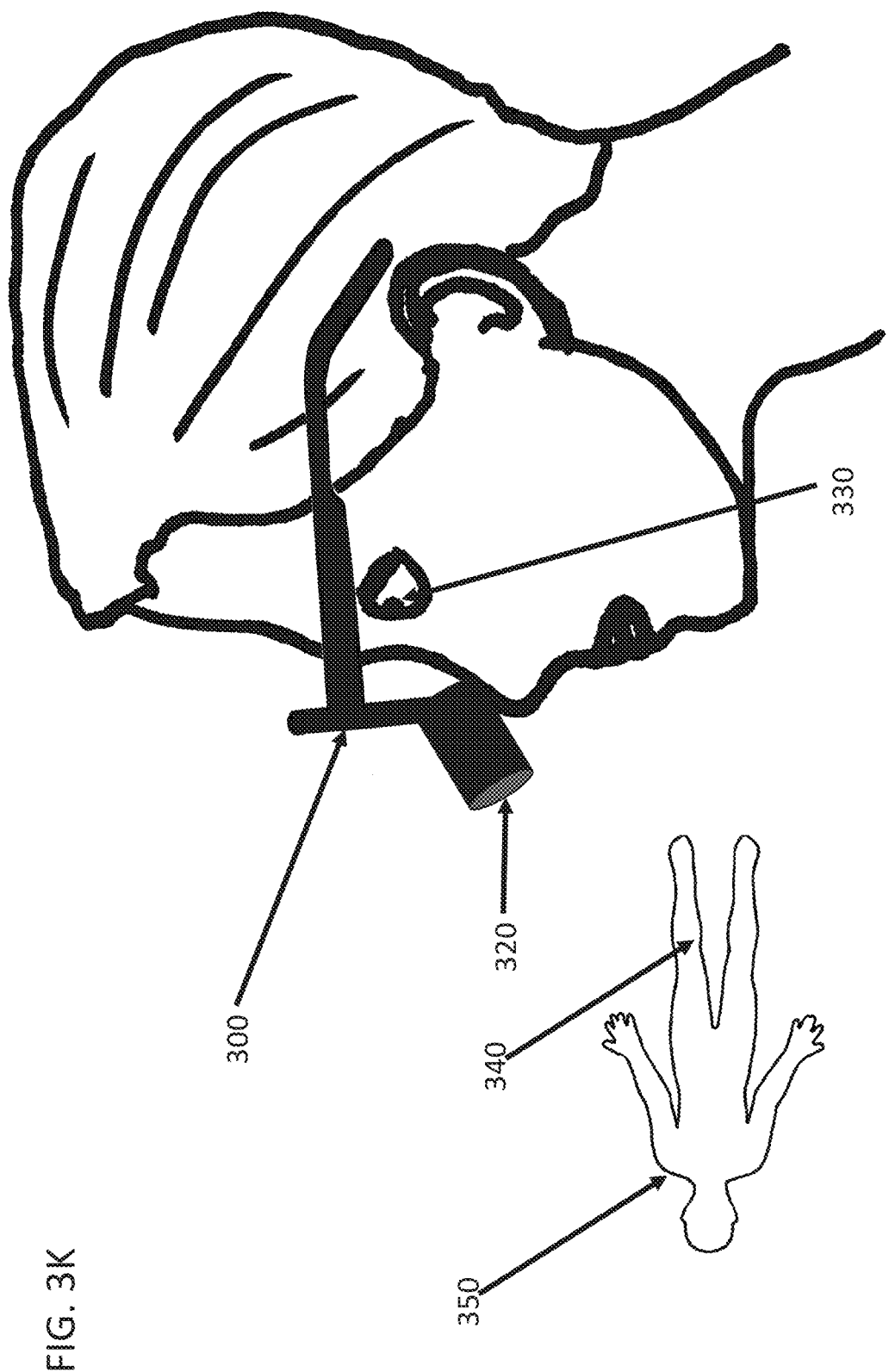
FIG. 3K illustrates an HMD used in conjunction with a surgical loupe, with the surgical loupe shown in a flipped down position relative to the user's eyes, according to various embodiments.

In some embodiments, a slidable and/or rotatable feature(s) are configured to move the loupe outside the field of view, e.g. away from an optical and/or visual axis of the user's eye, e.g. into an up position (FIG. 3J). In some embodiments, the loupe can be moved from a $1^{st}$ (e.g. down) position (FIG. 3I), e.g. pointing at an anatomic structure, to a $2^{nd}$ (e.g. up) position (FIG. 3J), for example to ensure an unobstructed view without a loupe located at the lower side of a user's field of view. The view through the loupe can be desirable when doing a decompression or bone removal or other fine repair or other surgical work (FIG. 3I). The view without loupe can be desirable when the loupe is not needed by the surgeon (FIG. 3J).

In some embodiments, a first, second, third, fourth or more locking or securing feature(s) or mechanism(s) are configured to lock and/or secure the loupe in a first position, e.g. aligned or substantially aligned with an optical and/or visual axis of the eye when directing the gaze towards the loupe, and/or to lock and/or secure the loupe in a second position, e.g. away from an optical and/or visual axis of the user's eye, e.g. into an up position, e.g. outside the field of view of the user's eyes and/or not aligned with a visual and/or optical axis of the eye(s). In some embodiments, a loupe is configured to be moved from the first to the second position. In some embodiments, the loupe is locked and/or secured (e.g. temporarily in the first and/or second position). In some embodiments, one or more locking or securing mechanisms are self-locking. In some embodiments, an HMD attachment (direct or indirect) to a head mount, a head mount frame, head mount housing, a head band, or a combination thereof comprises one or more features/mechanisms that are slideably engagable, e.g. a dovetail like feature/mechanism, a rail like feature/mechanism, a rod and piston like feature/mechanism.

In some embodiments, an HMD attachment (direct or indirect) to a head mount, a head mount frame, head mount housing, a head band, or a combination thereof comprises one or more features/mechanisms that are rotatably engagable, e.g. a hinge like feature/mechanism, a swivel like feature/mechanism, or any other rotation accommodating feature/mechanism.

In some embodiments, an HMD attachment (direct or indirect) to a head mount, a head mount frame, head mount housing, a head band or a combination thereof comprises one or more features/mechanisms that are rotatably and slideably engagable.

In some embodiments, the slideable and/or rotatable feature/mechanism comprises a first, a second, a third or more locking or securing features/mechanisms. For example, a screw, or any other locking or securing mechanism, can be utilized to lock a slideably engagable mechanism and/or feature at a predetermined or defined position, orientation, distance, angle, e.g. for locking and/or securing an HMD at a predetermined and/or defined height, distance, orientation, angle in relationship to an HMD attachment (direct or indirect) to a head mount, a head mount frame, head mount housing, at a predetermined or defined height and/or distance and/or angle relative to the user's eyes/cornea/pupil/retina/fovea, optical axis of the eye(s), visual axis of the eye(s) or a combination thereof.

In some embodiments, a slidable and/or rotatable feature are configured to move the HMD outside the field of view, e.g. away from an optical and/or visual axis of the user's eye, e.g. into an up position.

In some embodiments, a first, second, third, fourth or more locking or securing feature or mechanism are configured, for example to lock and/or secure the HMD in a first position, e.g. aligned with an optical and/or visual axis of the eye and at a desired eye relief when directing the gaze towards the HMD, and/or to lock and/or secure the HMD in a second position, e.g. away from an optical and/or visual axis of the user's eye, e.g. into an up position, e.g. outside the field of view of the user's eyes and/or not aligned with a visual and/or optical axis of the eye(s). In some embodiments, an HMD is configured to be moved from the first to the second position. In some embodiments, the HMD is locked and/or secured (e.g. temporarily in the first and/or second position). In some embodiments, one or more locking or securing mechanisms are self-locking.

Vertex Distance, Eye Relief, Eye Box, Field of View:

As used herein, eye relief (ER) 400 is the distance between the vertex of the last surface or back side or back surface of an optical combiner 480 (e.g. mirror, half-tone mirror, waveguide combiner, or other combiners) and the cornea 450 of a user's eye (see FIGS. 4A-4D). The last surface or back side or back surface of the combiner, as used herein, is the side of the combiner that is facing the user's eye and cornea.

As used herein, vertex distance VD 410 is distance between the base surface of a lens, e.g. an optional prescription lens 485 or other lens (e.g. the back facing lens of a loupe 490) at its vertex (eye side lens surface) and the tip of the cornea 450.

As used herein, eyebox is the 3D region located between a combiner 480 and the human eye pupil 455 over which the entire Field of View (FOV) is visible for a typical pupil size.

Figure 4A:
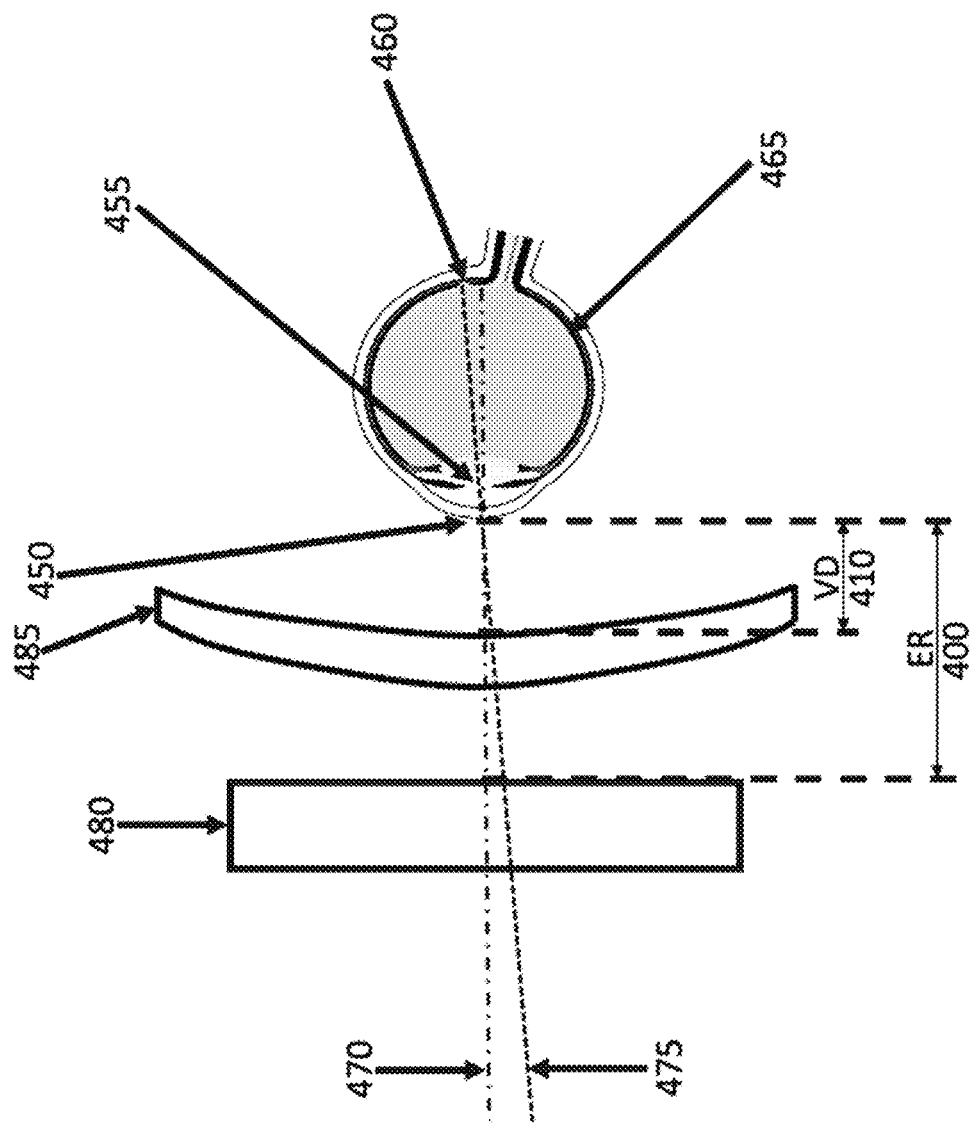
FIG. 4A illustrates a combiner of an HMD and a prescription lens placed in front of a user's eye, according to various embodiments.
Figure 4B:
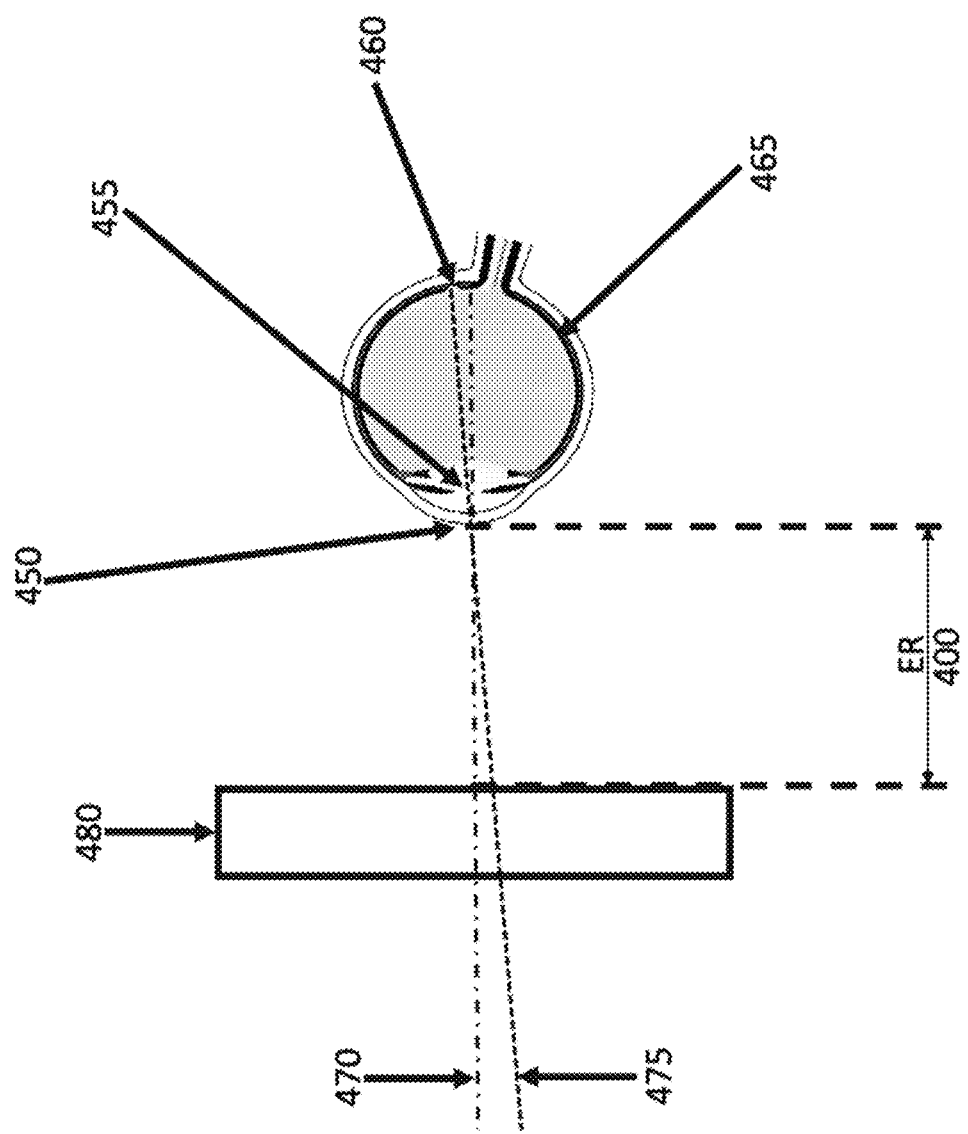
FIG. 4B illustrates a combiner of an HMD placed in front of a user's eye according to various embodiments.
Figure 4C:
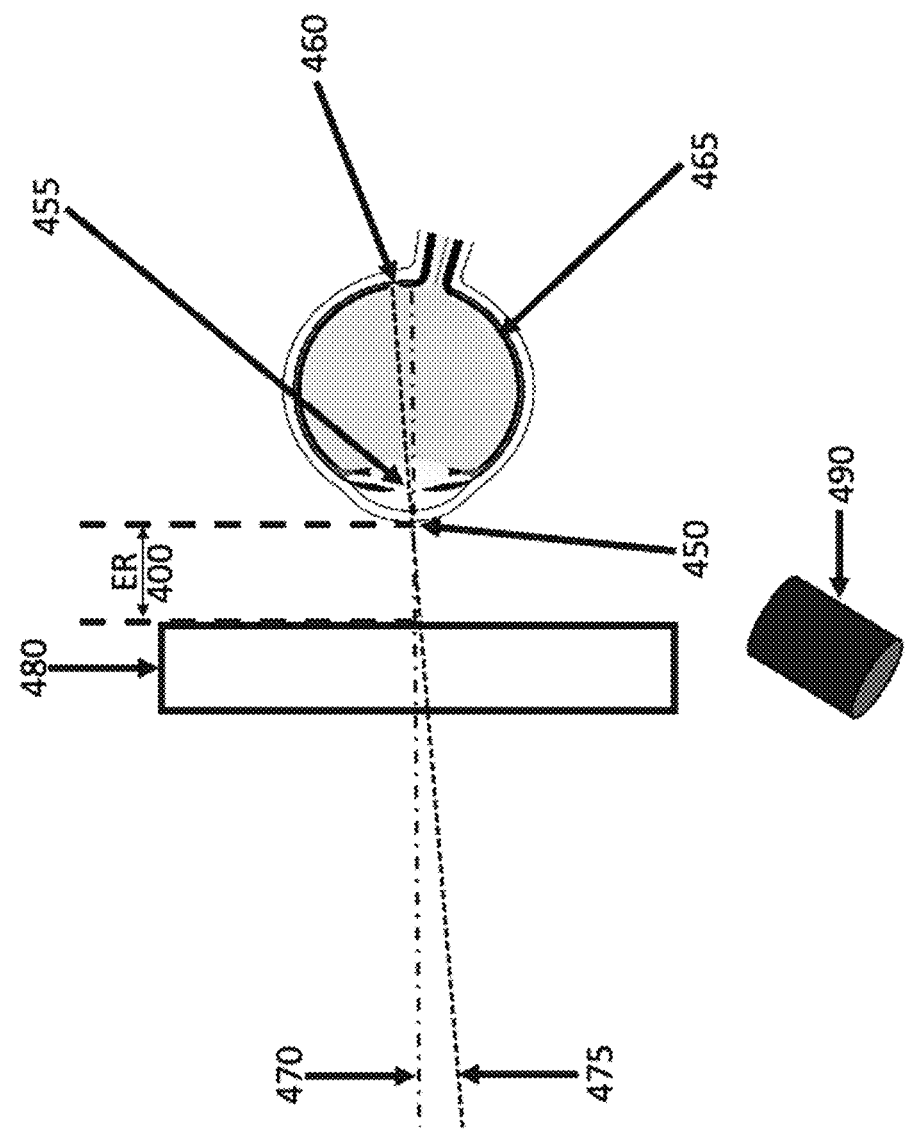
FIG. 4C illustrates a combiner of an HMD placed in front of a user's eye, with the system configured for concurrent use with a surgical loupe and the user looking through the HMD, according to various embodiments.
Figure 4D:
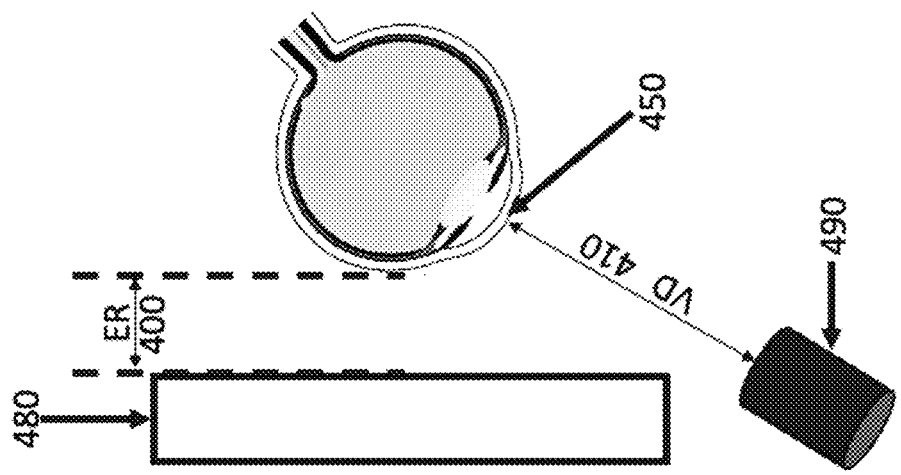
FIG. 4D illustrates an HMD placed in front of a user's eye, with the system configured for concurrent use with a surgical loupe and the user looking through the surgical loupe, according to various embodiments.

Field of view (FOV) is the angular range over which an image can be projected by the combiner. FIG. 4A is a non-limiting example of an HMD display with a combiner 480 used in conjunction with a prescription lens 485. FIG. 4B is a non-limiting example of an HMD display with a combiner 480 used without a prescription lens. FIGS. 4C and 4D are a non-limiting examples of an HMD display with a combiner 480 used in conjunction with a surgical loupe 490. The eye relief ER 400 between the tip of the cornea 450 and the back side of the combiner 480 as shown in FIG. 4C, with the user looking through the combiner 480 of the HMD display, is in this example smaller than the vertex distance VD 410 between the tip of the cornea 450 and the last lens of the loupe 490, when the user looking through the loupe 490. FIGS. 4A-4C also shows a fovea 460, a retina 465 of the human eye, as well as an optical axis 470 and a visual axis of the eye 475.

A vertex distance is the distance between the cornea of a user and a back surface of a lens, e.g. of a loupe, or, for example, a prescription lens or any other lens. In some embodiments, a vertex distance for a loupe is adjusted independent of an eye relief and/or eye box of an HMD. The vertex distance of a loupe can be optimized for facial features, facial shape, eye position, and position and/or orientation of an HMD display in relationship to the loupe. In some embodiments, the vertex distance of a loupe is adjusted and/or defined in relationship to an eye relief and/or an eye box of an HMD, and/or a cornea. The eye relief of an HMD is adjusted and/or defined in relationship to a cornea, a vertex distance of a loupe, a vertex distance of an interposed lens, e.g. a prescription lens, or a combination thereof. The vertex distance of a loupe and/or the eye relief of an HMD is adjusted and/or defined so as to minimize any potential reduction in the field of view of the HMD, the loupe, or a combination thereof. The vertex distance of a loupe and/or the eye relief of an HMD is adjusted and/or defined so as to minimize any potential reduction in the field of view of the HMD, the loupe, or a combination thereof and for a user's interpupillary distance and/or facial shape/features.

Figure 3L:
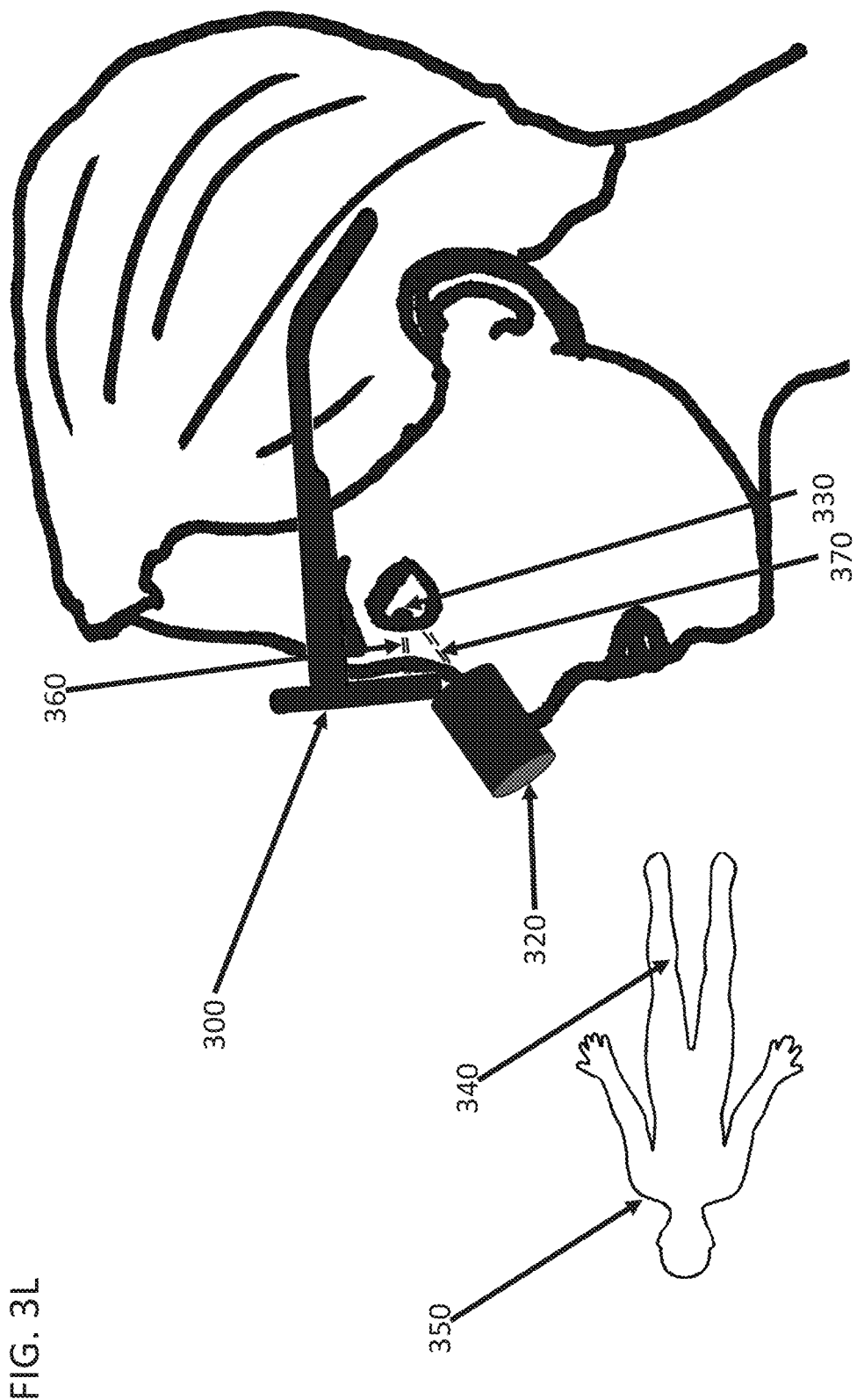
FIG. 3L illustrates an HMD used in conjunction with a surgical loupe, with the surgical loupe positioned in front of an HMD, according to various embodiments.

FIG. 3L is an additional non-limiting example showing a surgical loupe 320 mounted or attached in front of an HMD display 300 with a combiner. The eye relief 360 between the back surface of the combiner and the front surface of the cornea is smaller than the vertex distance 370 between the back lens of the surgical loupe 320 and the front surface of the cornea.

In some embodiments, a vertex distance for a loupe is adjusted independent of an eye relief of an HMD display. The vertex distance of a loupe can be optimized for facial features, shape, and/or a position and/or orientation of an HMD display and/or loupe. In some embodiments, the vertex distance of a loupe is adjusted and/or defined in relationship to an eye relief of an HMD, the eye relief of an HMD can be adjusted and/or defined in relationship to a vertex distance of a loupe, or a combination thereof. The vertex distance of a loupe and/or an eye relief of an HMD display can be adjusted and/or defined so as to minimize any potential reduction in the field of view of the HMD, the loupe, or a combination thereof. The vertex distance of a loupe and/or the eye relief of an HMD can be adjusted and/or defined so as to minimize any potential reduction in the field of view of the HMD, the loupe, or a combination thereof and for a user's interpupillary distance and/or facial shape/features.

In some embodiments, a system can be configured so that the vertex distance VD 410 from a cornea 450 to the back lens of a surgical loupe 490 is greater than the eye relief ER 400 between the cornea 450 and the back surface a combiner 480 of an HMD display. Without being bound to the theory, this configuration results in an optimization of, including a decrease, in eye relief ER 400 for the HMD display. A decreased eye relief, i.e. a decreased distance between the cornea 450 and the HMD combiner 480, typically increases the size of the eyebox, thereby allowing for viewing of the entire Field of View (FOV) of the HMD display.

Conversely, placing the HMD including the combiner 480 in front of the loupes 490, with the eye relief ER 400 greater than the vertex distance VD 410, increases the eye relief. An increased eye relief, i.e. an increased distance between the cornea 450 and the HMD combiner 480, typically decreases the size of the eyebox. A large eyebox is necessary to fit an HMD to a variety of users with a large range of a population's IPDs. In consequence, the perceived or visible FOV may be limited, display edges may be cut off and become invisible, and the 3D spatial experience may become compromised.

In addition, if the loupes are positioned directly in the line of sight of the HMD, the loupes will obstruct the field of view.

With a system configured with the vertex distance VD 410 from a cornea 450 to the back lens of a surgical loupe 490 greater than the eye relief ER 400 between the cornea 450 and the back surface a combiner 480 of an HMD display, it is possible that the field of view of the surgical loupe can become limited or restricted by the greater vertex distance; however, the user or surgeon can readily compensate for this by performing mild head movements to cover or view a larger area visible through the loupe. The head movements can be, for example, to the left and/or right, medial and/or lateral, superior and/or inferior, e.g. by 1 cm, 2 cm, 3 cm, 4 cm, 5 cm or more in one or more directions.

In some embodiments, a system comprises a head mounted display and a surgical loupe, wherein the head mounted display comprises a display unit with a combiner for the left eye and a display unit with a combiner for the right eye, wherein the surgical loupe comprises a left loupe for the left eye and a right loupe for the right eye, wherein the surgical loupe is mounted below the left eye display unit and the right eye display unit of the head mounted display, wherein the system is configured so that an eye relief from the back side of the left combiner to the front surface of the left cornea is the same or smaller than a vertex distance from the back lens of the left loupe to the front surface of the left cornea, or wherein the system is configured so that an eye relief from the back side of the right combiner to the front surface of the right cornea is the same or smaller than a vertex distance from the back lens of the right loupe to the front surface of the right cornea.

In some embodiments, the display unit, e.g. comprising a combiner, an LED display, an OLED display, optical and electronic components, of the HMD can be positioned at an optimal or near optimal distance relative to the user's eye (e.g. a cornea, pupil, retina, fovea). The distance can be a predetermined or desired eye relief, i.e. the distance from the front surface of the cornea to the back side of the display unit/combiner. The eye relief of the HMD can be 10-12 mm, 12-14 mm, 14-18 mm, 18-24 mm, 10-15 mm, 15-20 mm, 20-25 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, or any other value desired for an HMD display and/or a user.

In some embodiments, a vertex distance between the base surface of a lens, e.g. the back facing lens of a loupe, at its vertex (eye side lens surface) and the tip of the cornea can be 10-12 mm, 12-14 mm, 14-18 mm, 18-24 mm, 10-15 mm, 15-20 mm, 20-25 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, or any other value desired for a loupe and/or a user.

FIGS. 3A-3K are various non-limiting illustrative examples showing how a loupe and/or HMD can be moved in relationship to a user's eyes/pupil/retina/fovea, optical axis of the eye(s), visual axis of the eye(s) or a combination thereof and/or an anatomic structure of a patient. A loupe and/or HMD can be individually adjusted, also in relationship to each other and/or a user's eyes/pupil/retina/fovea, optical axis of the eye(s), visual axis of the eye(s) or a combination thereof and/or an anatomic structure of a patient.

In some embodiments, a locking or securing mechanism can comprise a "tang" feature with an entrance relief that has a slightly imposed interference to catch, for example, a loupe assembly. Another embodiment may utilize one or more magnets to secure the loupes in an up or down position. In another embodiment, latch like mechanisms can be used.

In some embodiments, an HMD and loupe assembly can comprise: An HMD adjustment mechanism configured to position, orient and/or align an HMD display in relationship to a user's pupil, cornea, retina, fovea, optical axis of the eye, visual axis of the eye or a combination thereof, wherein the HMD adjustment mechanism can comprise at least one first locking or securing feature, wherein the first locking or securing feature can be configured to lock or secure the HMD at a first defined position, orientation, and/or angle relative to the user's pupil, cornea, retina, fovea, optical axis of the eye, visual axis of the eye or a combination thereof, wherein the first defined position, orientation, and/or angle is configured to allow for viewing through the HMD; a loupe adjustment mechanism configured to position, orient and/or align a loupe in relationship to a user's pupil, cornea, retina, fovea, optical axis of the eye, visual axis of the eye or a combination thereof, wherein the loupe adjustment mechanism comprises at least one second locking or securing feature, wherein the second locking or securing feature is configured to lock or secure the loupe at a second defined position, orientation, and/or angle relative to the user's pupil, cornea, retina, fovea, optical axis of the eye, visual axis of the eye or a combination thereof, wherein the second defined position, orientation, and/or angle is configured to allow for viewing through the loupe, wherein the HMD adjustment mechanism and the loupe adjustment mechanism are configured to allow for viewing through the HMD at the first defined position, orientation, and/or angle and for viewing through the loupe at the second defined position, orientation, and/or angle without moving the HMD and the loupe, simply by re-directing the gaze from the HMD at the first defined position, orientation, and/or angle to the loupe at the second defined position, orientation, and/or angle or vice versa.

Any of the foregoing embodiments can comprise that directing the gaze comprises moving the eye, e.g. via activation of ocular muscles, to direct the user's pupil, cornea, retina, fovea, optical axis of the eye, visual axis of the eye or a combination thereof towards the HMD and/or the loupe. The eye movement can comprise aligning, at least partially, the user's pupil, cornea, retina, fovea, optical axis of the eye, visual axis of the eye or a combination thereof with an optical axis of the HMD, e.g. extending through the center of the HMD display or an area near the center of the HMD display, or an optical axis of the loupe, e.g. extending through the center of the loupe or an area near the center of the loupe. An example of eye movement ranges can be 45±7° in adduction, 45±7° in adduction, 28±8° in elevation, and 47±8° in depression. Other ranges are possible based on patient anatomy, age, and eye muscle function. Eye movement can also be described as up/right, right, down/right, down/left, left, and up/left, e.g. up approximately 45°, with a range, for example, from 35-55°, down approximately 45°, with a range, for example, from 35-55°, left approximately 45°, with a range, for example, from 20-55°, right approximately 45°, with a range, for example, from 20-55°, or combinations thereof including in oblique directions, e.g. up/right, down/right, up/left or down/left. In some embodiments, an HMD position and orientation and a surgical loupe position and orientation can be arranged or configured so that within the available eye movement range of a user, a user can look through the HMD display, display unit, combiner and through the surgical loupe. For example, a user can look approximately straight or slightly down through the HMD display, display unit, combiner (FIG. 4C) and, by directing the gaze down or down/left or down/right, through the surgical loupe (FIG. 4D). The optical or viewing axis of an HMD, HMD display unit and/or combiner can be at an angle of 10, 11, 12, 13, 14, 15, 16, 17, 18, 19, 20, 21, 22, 23, 24, 25, 28, 30, 32, 35, 40, 45, 50, 55, 60 degrees or any other value relative to the optical or viewing axis of the surgical loupe, e.g. in a sagittal plane or near sagittal plane. The angle between the optical or viewing axis of the HMD, HMD display unit and/or combiner and the surgical loupe (optionally left and right eye loupes) can be optimized for an eye movement range, e.g. an eye movement range of a user. The angle between the optical or viewing axis of the HMD, HMD display unit and/or combiner and the surgical loupe (optionally left and right eye loupes) can be adjustable for an eye movement range, e.g. an eye movement range of a user, and, once adjusted, can be optionally fixated at a selected angle for that user. The angle between the optical or viewing axis of the HMD, HMD display unit and/or combiner and the surgical loupe (optionally left and right eye loupes) can be adjusted, for example, within a range from 10-55 degrees, 15-50 degrees, 20-45 degrees, 25-45 degrees or any other range. The angle between the optical or viewing axis of the HMD, HMD display unit and/or combiner and the surgical loupe (optionally left and right eye loupes) can be adjusted, for example, over a range of 50 degrees, 45 degrees, 40 degrees, 35 degrees, 30 degrees, 25 degrees, 20 degrees, 15 degrees, 12 degrees, or any other range.

The HMD display can have an HMD display unit or a combiner for the left eye and an HMD display unit or a combiner the right eye. The surgical loupe can have a loupe for the left eye and a loupe for the right eye. The left eye and the right eye HMD display unit or combiner can have a convergence, which can be optionally adjustable, e.g. for a given distance to an anatomic structure. The left eye and the right eye loupe can have a convergence, which can be optionally adjustable, e.g. for a given distance to an anatomic structure. The convergence of the left eye and the right eye HMD display unit or combiner and/or the surgical loupe can be fixated at a predetermined value, e.g. for an estimated distance to an anatomic structure. The left eye and the right eye HMD display unit or combiner can have a convergence that is the same or substantially the same as or similar to the convergence of the left eye and the right eye loupe. The difference between the convergence of the left eye and the right eye HMD display unit or combiner and the convergence of the left eye and the right eye loupe can be less than 5 degrees, 4 degrees, 3 degrees, 2 degrees, 1 degree, 0.5 degrees, 0.2 degrees, 0.1 degrees or any other value.

The left eye HMD display unit or combiner and the right eye HMD display unit or combiner, each can have a convergence that is greater than the convergence of the left eye and the right eye loupe, e.g. by 0.5 degrees, 1 degree, 2 degrees, 3 degrees, 4 degrees, 5 degrees, 6 degrees, 7 degrees, 8 degrees, 9 degrees, 10 degrees or any other value. The left eye and the right eye HMD display unit or combiner can have a convergence that is less than the convergence of the left eye and the right eye loupe, e.g. by 0.5 degrees, 1 degree, 2 degrees, 3 degrees, 4 degrees, 5 degrees, 6 degrees, 7 degrees, 8 degrees, 9 degrees, 10 degrees or any other value.

In some embodiments, the optical axis of the HMD or the optical axis of the loupe intersects the user's pupil, cornea, retina, fovea, or combination thereof.

In some embodiments, the optical axis of the HMD or the optical axis of the loupe intersects the center of the user's pupil, cornea, retina, fovea, or combination thereof.

In some embodiments, the optical axis of the HMD or the optical axis of the loupe intersects the user's pupil, cornea, retina, fovea, or combination thereof near their center, e.g. 0.5, 1.0, 1.5, 2.0, 2.5, 3.0 mm or any other value from the center.

In some embodiments, the optical axis of the HMD or the optical axis of the loupe are parallel and/or tangent with the optical axis of the eye, visual axis of the eye or a combination thereof.

In some embodiments, the optical axis of the HMD or the optical axis of the loupe are substantially parallel and/or tangent with the optical axis of the eye, visual axis of the eye or a combination thereof.

In some embodiments, the optical axis of the HMD or the optical axis of the loupe intersects the optical axis of the eye, visual axis of the eye or a combination thereof. For example, the optical axis of the HMD or the optical axis of the loupe can be at an angle with the optical axis of the eye, visual axis of the eye or a combination thereof. The angle can be, for example, in a range where the visual field of the HMD or the loupe is not cut off for the user or is only partially cut off, e.g. 3%, 5%, 7%, 10% or any other value. The angle can be 1, 2, 3, 4, 5, 6, 7, 8, 9, 10 degrees or any other value.

Virtual Displays

Virtual displays as used in some embodiments are described in U.S. Pat. No. 9,861,446 issued Jan. 9, 2018, and U.S. Pat. No. 11,727,581, which are hereby incorporated by reference in their entirety. A virtual display can be a 2D display, a 3D display, a non-stereoscopic display, a stereoscopic display, or a combination thereof.

A virtual display can comprise a 2D image of an anatomic structure of a patient, a 3D image of an anatomic structure of a patient, a virtual tool, a virtual instrument, a virtual implant, a virtual device, or a combination thereof, as described in U.S. Pat. Nos. 9,861,446, and 11,727,581, which are hereby incorporated by reference in their entirety. One or more computer processors can be configured to generate a virtual display. In some embodiments, a virtual display can comprise, for example, one or more of a virtual surgical tool, virtual surgical instrument, virtual surgical guide, virtual cut block, virtual trial implant, virtual implant component, virtual implant or virtual device, one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration. A virtual display can comprise a virtual interface. With a virtual interface projected by an HMD a surgeon or user can move a virtual arrow up or down or left or right to scroll images backward or forward or, for example, to rotate the images or to display them in different multiplanar angles or to change the view angle or projection angle. A virtual interface can comprise a virtual button or virtual fields, as described in detail in U.S. Pat. No. 9,861,446 B2 issued Jan. 9, 2018, and U.S. Pat. No. 11,727,581 B2 issued on Aug. 15, 2023, which are hereby incorporated by reference in their entirety.

Eye Tracking Systems

In some embodiments, the system includes an eye tracking system. The eye tracking system can be integrated into an HMD. Different types of eye tracking systems can be utilized. The examples provided below are in no way thought to be limiting to the disclosure. Any eye tracking system known in the art now can be utilized.

Eye movement can be divided into fixations and saccades—when the eye gaze pauses in a certain position, and when it moves to another position, respectively. The resulting series of fixations and saccades can be defined as a scan path. The central one or two degrees of the visual angle provide most of the visual information; the input from the periphery is less informative. Thus, the locations of fixations along a scan path show what information locations were processed during an eye tracking session, for example during a surgical procedure.

Eye trackers can measure rotation or movement of the eye in several ways, for example via measurement of the movement of an object (for example, a form of contact lens) attached to the eye, optical tracking without direct contact to the eye, and measurement of electric potentials using electrodes placed around the eyes.

If an attachment to the eye is used, it can, for example, be a special contact lens with an embedded mirror or magnetic field sensor. The movement of the attachment can be measured with the assumption that it does not slip significantly as the eye rotates. Measurements with tight fitting contact lenses can provide very accurate measurements of eye movement. Additionally, magnetic search coils can be utilized which allow measurement of eye movement in horizontal, vertical and torsion direction.

Alternatively, non-contact, optical methods for measuring eye motion can be used. With this technology, light, optionally infrared, can be reflected from the eye and can be sensed by an optical sensor or a video camera. The information can then be measured to extract eye rotation and/or movement from changes in reflections.

Optical sensor or video-based eye trackers can use the corneal reflection (the so-called first Purkinje image) and the center of the pupil as features to track, optionally over time. A more sensitive type of eye tracker, the dual-Purkinje eye tracker, uses reflections from the front of the cornea (first Purkinje image) and the back of the lens (fourth Purkinje image) as features to track. An even more sensitive method of tracking is to image features from inside the eye, such as the retinal blood vessels, and follow these features as the eye rotates and or moves. Optical methods, particularly those based on optical sensors or video recording, can be used for gaze tracking.

In some embodiments, the system comprises optical or video-based eye trackers. A camera focuses on one or both eyes and tracks their movement as the viewer performs a function such as a surgical procedure. The eye-tracker can use the center of the pupil for tracking. Infrared or near-infrared non-collimated light can be utilized to create corneal reflections. The vector between the pupil center and the corneal reflections can be used to compute the point of regard on a surface or the gaze direction. Optionally, a calibration procedure can be performed at the beginning of the eye tracking.

Bright-pupil and dark-pupil eye tracking can be employed. Their difference is based on the location of the illumination source with respect to the optics. If the illumination is co-axial relative to the optical path, then the eye acts is retroreflective as the light reflects off the retina creating a bright pupil effect similar to a red eye. If the illumination source is offset from the optical path, then the pupil appears dark because the retroreflection from the retina is directed away from the optical sensor or camera.

Bright-pupil tracking can have the benefit of greater iris/pupil contrast, allowing more robust eye tracking with all iris pigmentation. It can also reduce interference caused by eyelashes. It can allow for tracking in lighting conditions that include darkness and very bright lighting situations.

The optical tracking method can include tracking movement of the eye including the pupil as described above. The optical tracking method can also include tracking of the movement of the eye lids and also periorbital and facial muscles.

In some embodiments, the eye-tracking apparatus is integrated in an optical head mounted display. In some embodiments, head motion is simultaneously tracked, for example using a combination of accelerometers and gyroscopes forming an inertial measurement unit (see below).

In some embodiments, electric potentials are measured with electrodes placed around the eyes. The eyes generate an electric potential field, which can also be detected if the eyes are closed. The electric potential field can be modelled to be generated by a dipole with the positive pole at the cornea and the negative pole at the retina. It can be measured by placing two electrodes on the skin around the eye. The electric potentials measured in this manner are called an electro-oculogram.

If the eyes move from the center position towards the periphery, the retina approaches one electrode while the cornea approaches the opposing one. This change in the orientation of the dipole and consequently the electric potential field results in a change in the measured electro-oculogram signal. By analyzing such changes eye movement can be assessed. Two separate movement directions, a horizontal and a vertical, can be identified. If a posterior skull electrode is used, a EOG component in radial direction can be measured. This is typically the average of the EOG channels referenced to the posterior skull electrode. The radial EOG channel can measure saccadic spike potentials originating from extra-ocular muscles at the onset of saccades.

EOG can be limited for measuring slow eye movement and detecting gaze direction. EOG is, however, well suited for measuring rapid or saccadic eye movement associated with gaze shifts and for detecting blinks. Unlike optical or video-based eye-trackers, EOG allows recording of eye movements even with eyes closed. The major disadvantage of EOG is its relatively poor gaze direction accuracy compared to an optical or video tracker. Optionally, both methods, optical or video tracking and EOG, can be combined in select embodiments of the disclosure.

A sampling rate of 15, 20, 25, 30, 50, 60, 100, 120, 240, 250, 500, 1000 Hz or greater can be used. Any sampling frequency is possibly. In many embodiments, sampling rates greater than 30 Hz will be preferred.

In some embodiments, the eye tracking is configured to determine when the user looks towards the center or near the center of an HMD. In some embodiments, eye tracking can be used to determine when the user looks towards the center or near the center of a loupe. In some embodiments, the system comprises a computer processor configured to turn on the HMD display when the user looks towards the center or near the center of an HMD. In some embodiments, the system comprises a computer processor configured to turn off the HMD display when the user looks towards the center or near the center of the loupe. In some embodiments, at least portions or select display components of an HMD display can be turned on or off based on eye tracking information, e.g. when eye tracking determines a surgeon/user is looking in the direction of a loupe and/or HMD or away from the direction of a loupe and/or HMD. In some embodiments, a lower, inferior portion of the HMD display can be turned on or off based on eye tracking information, e.g. when eye tracking determines a surgeon/user is looking in the direction of a loupe and/or HMD or away from the direction of a loupe and/or HMD. In some embodiments, other portions of the HMD display can be turned on or off based on eye tracking information, e.g. when eye tracking determines a surgeon/user is looking in the direction of a loupe and/or HMD or away from the direction of a loupe and/or HMD.

In some embodiments, the system comprises a head mounted display (HMD), and a surgical loupe. In some embodiments, the head mounted display comprises a display unit with a combiner. In some embodiments, the surgical loupe is mounted below the display unit of the head mounted display. In some embodiments, eye relief from the back side of the combiner to the front surface of the cornea is the same or smaller than a vertex distance from the back lens of the surgical loupe to the front surface of the cornea.

In some embodiments, the system comprises a head mounted display (HMD), and a surgical loupe, the head mounted display comprising a display unit with a combiner, wherein the surgical loupe is mounted below the display unit of the head mounted display, and wherein eye relief from the back side of the combiner to the front surface of the cornea is the same or smaller than a vertex distance from the back lens of the surgical loupe to the front surface of the cornea.

In some embodiments, the surgical loupe is attached to the head mounted display, to a head mount, or to a head band.

In some embodiments, the display unit of the HMD comprises at least one LED display, OLED display, optical element, electronic element, the combiner or combination thereof.

In some embodiments, the combiner comprises a mirror, a halftone mirror, a curved mirror, a waveguide or combination thereof.

In some embodiments, the display unit is configured to generate, display, and/or reflect a virtual display. In some embodiments, the virtual display is a 2D display, a 3D display, a non-stereoscopic display, a stereoscopic display, or a combination thereof. In some embodiments, the virtual display comprises a 2D image of an anatomic structure of a patient, a 3D image of an anatomic structure of a patient, a virtual tool, a virtual instrument, a virtual implant, a virtual device, or a combination thereof.

In some embodiments, the system further comprises an attachment mechanism, wherein the attachment mechanism is configured to attach the surgical loupe to the head mounted display, the head mount or the head band. In some embodiments, the attachment mechanism is configured to move the loupe into at least a first and a second position in relationship to the head mounted display. In some embodiments, the first position is configured to facilitate viewing through the surgical loupe, wherein the second position is configured to place the loupe outside the visual field of the user.

In some embodiments, the HMD is an optical see through head mounted display.

In some embodiments, the system is configured to be worn on a head of a user.

Aspects of the disclosure relate to system comprising: a head mounted display; and a surgical loupe, wherein the head mounted display comprises a display unit with a combiner for the left eye and a display unit with a combiner for the right eye, wherein the surgical loupe comprises a left surgical loupe for the left eye and a right surgical loupe for the right eye, wherein the left surgical loupe is mounted below the left eye display unit and the right surgical loupe below the right eye display unit of the head mounted display, and wherein an eye relief from the back side of the left combiner to the front surface of the left cornea is the same or smaller than a vertex distance from the back lens of the left loupe to the front surface of the left cornea, and/or wherein an eye relief from the back side of the right combiner to the front surface of the right cornea is the same or smaller than a vertex distance from the back lens of the right loupe to the front surface of the right cornea.

In some embodiments, the left surgical loupe and the right surgical loupe are attached to the head mounted display, to a head mount, or to a head band.

In some embodiments, each display unit of the HMD comprises at least one LED display, OLED display, optical element, electronic element, or combination thereof.

In some embodiments, each combiners comprises a mirror, a halftone mirror, a curved mirror, a waveguide or combination thereof.

In some embodiments, each display unit is configured to generate, display, and/or reflect a virtual display. In some embodiments, the virtual display is a 2D display, a 3D display, a non-stereoscopic display, a stereoscopic display, or a combination thereof. In some embodiments, the virtual display comprises a 2D image of an anatomic structure of a patient, a 3D image of an anatomic structure of a patient, a virtual tool, a virtual instrument, a virtual implant, a virtual device, or a combination thereof.

In some embodiments, the system further comprises one or more attachment mechanism, wherein the one or more attachment mechanism is configured to attach the left surgical loupe and the right surgical loupe to the head mounted display, the head mount or the head band. In some embodiments, the one or more attachment mechanism is configured to move the left surgical loupe into at least a first and a second position in relationship to the head mounted display, and/or to move the right surgical loupe into at least a first and a second position in relationship to the head mounted display. In some embodiments, the first position is configured to facilitate viewing through the left surgical loupe and/or the right surgical loupe, wherein the second position is configured to place the left surgical loupe and/or the right surgical outside the visual field of the user.

All patents, patent applications, and published references cited herein are hereby incorporated by reference in their entirety.

The invention claimed is:

1. A system comprising:
a head mounted display (HMD);
a surgical loupe; and
an attachment mechanism,
wherein the head mounted display comprises a display unit with a combiner,
wherein the surgical loupe is mounted below the display unit of the head mounted display,
wherein the attachment mechanism is configured to attach the surgical loupe to the head mounted display, the head mount or the head band,
wherein the attachment mechanism is configured to move the surgical loupe into at least a first and a second position in relationship to the head mounted display, and
wherein an eye relief from a back side of the combiner to a front surface of a cornea is the same or smaller than a vertex distance from a back lens of the surgical loupe to the front surface of the cornea.

2. The system of claim 1, wherein the display unit of the HMD comprises at least one LED display, OLED display, optical element, electronic element, the combiner or combination thereof.

3. The system of claim 1, wherein the combiner comprises a mirror, a halftone mirror, a curved mirror, a waveguide or combination thereof.

4. The system of claim 1, wherein the display unit is configured to display a virtual display.

5. The system of claim 4, wherein the virtual display is a 2D display, a 3D display, a non-stereoscopic display, a stereoscopic display, or a combination thereof.

6. The system of claim 5, wherein the virtual display comprises a 2D image of an anatomic structure of a patient, a 3D image of an anatomic structure of a patient, a virtual tool, a virtual instrument, a virtual implant, a virtual device, or a combination thereof.

7. The system of claim 1, wherein the first position is configured to facilitate viewing through the surgical loupe, wherein the second position is configured to place the loupe outside the visual field of a user wearing the system.

8. The system of claim 1, wherein the display unit is configured to reflect a virtual display.

9. A system comprising: a head mounted display (HMID); and a surgical loupe; and one or more attachment mechanism wherein the head mounted display comprises a display unit with a left combiner for the left eye and a display unit with a right combiner for the right eye, wherein the surgical loupe comprises a left surgical loupe for a left eye and a right surgical loupe for a right eye, wherein the left surgical loupe is mounted below the left eye display unit and the right surgical loupe below the right eye display unit of the head mounted display, wherein the one or more attachment mechanism is configured to attach the left surgical loupe and the right surgical loupe to the head mounted display, the head mount or the head band, wherein the one or more attachment mechanism is configured to move the left surgical loupe into at least a first and a second position in relationship to the head mounted display, and to move the right surgical loupe into at least a first and a second position in relationship to the head mounted display, wherein the first position is configured to facilitate viewing through the left surgical loupe and or the right surgical loupe, wherein the second position is configured to place the left surgical loupe and the right surgical outside the visual field of a user wearing the system, wherein an eye relief from back side of the left combiner to a front surface of a left cornea is the same or smaller than a vertex distance from a back lens of the left loupe to the front surface of the left cornea, and wherein an eye relief from a back side of the right combiner to the front surface of the right cornea is the same or smaller than a vertex distance from a back lens of the right loupe to the front surface of the right cornea.

10. The system of claim 9, wherein each display unit of the HMD comprises at least one LED display, OLED display, optical element, electronic element, or combination thereof.

11. The system of claim 9, wherein each combiner comprises a mirror, a halftone mirror, a curved mirror, a waveguide or combination thereof.

12. The system of claim 9, wherein each display unit is configured to display a virtual display.

13. The system of claim 12, wherein the virtual display is a 2D display, a 3D display, a non-stereoscopic display, a stereoscopic display, or a combination thereof.

14. The system of claim 13, wherein the virtual display comprises a 2D image of an anatomic structure of a patient, a 3D image of an anatomic structure of a patient, a virtual tool, a virtual instrument, a virtual implant, a virtual device, or a combination thereof.

15. The system of claim 9, wherein each display unit is configured to reflect a virtual display.

16. A system comprising: a head mounted display (HMD); a surgical loupe; and one or more attachment mechanism; wherein the head mounted display comprises a display unit with a left combiner for the left eye and a display unit with a right combiner for the right eye, wherein the surgical loupe comprises a left surgical loupe for a left eye and a right surgical loupe for a right eye, wherein the left surgical loupe is mounted below the left eye display unit and the right surgical loupe below the right eye display unit of the head mounted display, wherein the one or more attachment mechanism is configured to attach the left surgical loupe and the right surgical loupe to the head mounted display, the head mount or the head band, wherein the one or more attachment mechanism is configured to move the left surgical loupe into at least a first and a second position in relationship to the head mounted display, and to move the right surgical loupe into at least a first and a second position in relationship to the head mounted display, wherein the first position is configured to facilitate viewing through the left surgical loupe and the right surgical loupe, wherein the second position is configured to place the left surgical loupe and the right surgical outside the visual field of a user wearing the system, and wherein an eye relief from a back side of the right combiner to the front surface of the right cornea is the same or smaller than a vertex distance from a back lens of the right loupe to the front surface of the right cornea.

* * * * *